United States Patent [19]

Miller

[11] Patent Number: 5,559,132

[45] Date of Patent: Sep. 24, 1996

[54] CARBOXAMIDE DERIVATIVES FOR TREATING ASTHMA

[75] Inventor: Scott C. Miller, Wilmington, Del.

[73] Assignee: Zeneca Limited, London, United Kingdom

[21] Appl. No.: 392,013

[22] Filed: Feb. 21, 1995

Related U.S. Application Data

[60] Division of Ser. No. 148,184, Nov. 3, 1993, which is a continuation-in-part of Ser. No. 971,141, Nov. 3, 1992, abandoned.

[30] Foreign Application Priority Data

Jul. 16, 1993 [GB] United Kingdom ............... 9314783

[51] Int. Cl.[6] .................. A61K 31/445; C07D 211/58; C07D 211/72; C07D 401/04
[52] U.S. Cl. ................... 514/329; 514/326; 546/194; 546/208; 546/223; 546/224
[58] Field of Search ................... 846/208, 224, 846/223; 514/326, 329

[56] References Cited

U.S. PATENT DOCUMENTS

| | | | |
|---|---|---|---|
| 3,371,093 | 2/1968 | Zenitz et al. | 546/224 |
| 4,105,771 | 8/1978 | Archibald et al. | 546/224 |
| 4,167,574 | 9/1979 | Janssens | 514/329 |
| 5,169,856 | 12/1992 | Goto et al. | 514/331 |
| 5,232,978 | 8/1993 | Gottschlich et al. | 514/252 |
| 5,236,921 | 8/1993 | Emonds-Alt et al. | 514/252 |
| 5,300,648 | 4/1994 | Edmonds Alt et al. | 546/193 |
| 5,340,822 | 8/1994 | Edmonds-Alt et al. | 514/316 |
| 5,411,971 | 5/1995 | Edmonds-Alt et al. | 514/318 |

FOREIGN PATENT DOCUMENTS

| | | |
|---|---|---|
| 2029275 | 5/1991 | Canada . |
| 2067924 | 11/1992 | Canada . |
| 2090785 | 9/1993 | Canada . |
| 428434 | 5/1991 | European Pat. Off. . |
| 474561 | 3/1992 | European Pat. Off. . |
| 515240 | 11/1992 | European Pat. Off. . |
| 559538 | 9/1993 | European Pat. Off. . |
| 923177 | 1/1993 | South Africa . |
| 923178 | 1/1993 | South Africa . |
| 95/05377 | 2/1995 | WIPO . |

OTHER PUBLICATIONS

Emonds-Alt et al., "Preparation of 1—(alkyl— or acyl)—4—(3—aryl—4—aminobutyl) piperidines as substance P receptor binding inhibitors", *Chemical Abstracts* (1993), vol. 118, No. 13, 124404.

Goulaouic et al., "Preparation of 1—aralk(ano)yl—3—aryl—3— (piperidinoalkyl) piperidines and analogs as substance P and neurokinin antagonists", *Chemical Abstracts* (1993), vol. 118, No. 13, 124405k.

Fujii et al., "Effects of actinomycin D on airway constriction reduced by tachyknins", BA (1991) 91:124844.

X. Edmonds-Alt et al., "Pharmacological Profile and Chemical Synthesis of SR 48968, a Non-Peptide Antagonist of the Neurokinin A ($NK_2$) Receptor", *Biorganic & Medicinal Chemistry Letters*, (1993), vol. 3, No. 5, 925–930.

Burger "A guide to the chemical basis of drug design" John Wiley & Sons p.15, (1984).

*Primary Examiner*—Ceila Chang
*Attorney, Agent, or Firm*—Robert J. Harris

[57] ABSTRACT

The present invention concerns novel carboxamide derivatives of formula I, set out hereinbelow which antagonize the pharmacological actions of one of the endogenous neuropeptide tachykinins at the neurokinin 2 (NK2) receptor, making them useful whenever such antagonism is desired, such as in the treatment of asthma and related conditions. The invention also provides pharmaceutical compositions containing the novel carboxamide derivatives for use in such treatment, methods for their use, and processes and intermediates for the manufacture of the novel carboxamide derivatives.

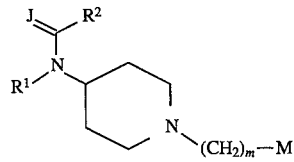

11 Claims, 3 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GCGCAAGCTT ATGGG                                      15

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GTCCCCATAA GCTTGCGC                                 18

CARBOXAMIDE DERIVATIVES FOR TREATING ASTHMA

This is a divisional of co-pending application Ser. No. 08/148,184, filed Nov. 3, 1993, which application is a continuation-in-part of U.S. Ser. No. 07/971,141, filed Nov. 3, 1992, now abandoned.

This invention concerns novel carboxamide derivatives, and, more particularly, novel N-substituted benzamide derivatives which antagonize the pharmacological actions of one of the endogenous neuropeptide tachykinins known as neurokinins, particularly at the neurokinin 2 (NK2) receptor. The novel carboxamide derivatives are useful whenever such antagonism is desired. Thus, such compounds may be of value in the treatment of those diseases in which an NK2 receptor is implicated, for example, in the treatment of asthma and related conditions. The invention also provides pharmaceutical compositions containing the novel carboxamide derivatives for use in such treatment, methods for their use, and processes and intermediates fox the manufacture of the novel carboxamide derivatives.

The mammalian neurokinins comprise a class of peptide neurotransmitters which are found in the peripheral and central nervous systems. The three principal neurokinins are Substance P (SP), Neurokinin A (NKA) and Neurokinin B (NKB). There are also N-terminally extended forms of at least NKA. At least three receptor types are known for the three principal neurokinins. Based upon their relative selectivities favoring the neurokinin agonists SP, NKA and NKB, respectively, the receptors are classifed as neurokinin 1 (NK1), neurokinin 2 (NK2) and neurokinin 3 (NK3) receptors, respectively. In the periphery, SP and NKA are localized in C-afferent sensory neurons, which neurons are characterized by non-myelinated nerve endings known as C-fibers, and are released by selective depolarization of these neurons, or selective stimulation of the C-fibers. C-Fibers are located in the airway epithelium, and the tachykinins are known to cause profound effects which clearly parallel many of the symptoms observed in asthmatics. The effects of release or introduction of tachykinins in mammalian airways include bronchoconstriction, increased microvascular permeability, vasodilation and activation of mast cells. Thus, the tachykinins are implicated in the pathophysiology and the airway hyperresponsiveness observed in asthmatics; and blockade of the action of released tachykinins may be useful in the treatment of asthma and related conditions. Peptidic NK2 antagonists have been reported. For example, a cyclic hexapeptide known as L-659,877 has been reported as a selective NK2 antagonist. Nonpeptidic NK2 antagonists also have been reported, for example in European Patent Application, Publication Number (EPA) 428434 and EPA 474561 (U.S. counterpart Pat. No. 5,236,921). I have discovered a series of nonpeptidic NK2 antagonists, and this is the basis for my invention. Subsequently, further nonpeptidic NK2 antagonists have been disclosed in EPA 512901, EPA 512902 and EPA 515240 (with counterparts including the Canadian (CA) applications CA 2,067,877; CA 2,067,834 and CA 2,067,924, respectively, each with the publication date of Nov. 4, 1992), as well as in EPA 559538 (with an earlier Hungarian counterpart HU 9300580, published May 28, 1993). In EPA 515240, there are disclosed certain compounds corresponding to the below disclosed compounds of formula I in which M is of formula Ia (and corresponding compounds of formula Ic) wherein J is oxygen; $R^1$ is phenyl (unsubstituted or substituted one or more times with a halogen atom, with a (1-3C)alkyl, with a trifluoromethyl, with a (1-3C)alkoxy or with a hydroxy) or $R^1$ is pyridyl; and $R^2$ is (1-3C)alkyl. The species described below as Example 6 also is disclosed in EPA 515240.

According to the invention, there is provided a Compound of the invention which is a compound of formula I (formula set out hereinbelow following the Examples, together with other formulae denoted by Roman numerals) wherein J is oxygen, sulfur or $NR^n$ in which $R^n$ is hydrogen or (1-5C)alkyl;

$R^1$ is hydrogen, (1-6C)alkyl, (3-6C)alkenyl (in which a vinyl carbon is not bound to nitrogen), 2-hydroxyethyl, (3-7C)cyloalkyl, phenyl or a 6-membered heteroaryl containing one or two nitrogens as the heteroatom(s) in which the phenyl or heteroaryl group may bear one or more substituents independently selected from halo, trifluoromethyl, (1-4C)alkyl, (1-4C)alkoxy, nitro, amino and hydroxy;

$R^2$ is hydrogen, (1-6C)alkyl which may bear a hydroxy substituent and/or one to three fluoro substituents, (3-6C)cycloalkyl, (1-5C)alkoxy (only when J is oxygen), (3-6C)cycloalkyloxy (only when J is oxygen), or an amino group of formula $NR^aR^b$ containing zero to about seven carbon atoms in which each of $R^a$ and $R^b$ is independently hydrogen, (1-5C)alkyl or (3-6C)cycloalkyl, or $R^a$ and $R^b$ together with the nitrogen to which they are attached form a pyrrolidino, piperidino, morpholino, thiomorpholino (or its S-oxide) or piperazinyl group (which piperazinyl group may bear a methyl or ethyl group at the 4-position); or $R^1$ and $R^2$ together form a divalent hydrocarbon group L in which the 1-position is bound to the carbon bearing the group J, the divalent group L being selected from trimethylene, cis-propenylene, tetramethylene, cis-butenylene, cis-but-3-enylene, cis,cis-butadienylene, pentamethylene and cis-pentenylene which divalent group L itself may bear one or two methyl substituents;

m is 2 or 3;

M is a residue of formula Ia or formula Ib wherein

Q is phenyl which may bear one or two substituents independently selected from halo, trifluoromethyl, hydroxy, (1-3C)alkoxy, (1-3C)alkyl and methylenedioxy; or Q is thienyl, imidazolyl, benzo[b]thiophenyl or naphthyl any of which may bear a halo substituent; or Q is biphenylyl; or Q is carbon-linked indolyl which may bear a benzyl substituent at the 1-position;

$Q^a$ is hydrogen, (1-4C)alkyl, or a radical of formula $—(CH_2)_q—NR^7R^8$ in which q is 2 or 3 and $R^7$ and $R^8$ are independently (1-4C)alkyl or $NR^7R^8$ is piperidino or 4-benzylpiperidino;

$R^3$ is hydrogen, methyl or (2-6C)n-alkyl which may bear a terminal amino radical;

$R^4$ is $—COR^5$, $—COOR^5$ or $—C(=J^1)NHR^5$ in which $J^1$ is oxygen or sulfur and $R^5$ is hydrogen, (1-6C)alkyl, phenyl(1-3C)alkyl (in which the phenyl may bear one or more halo, hydroxy, (1-4C)alkoxy or (1-4C)alkyl substituents), pyridyl(1-3C)alkyl, naphthyl(1-3C)alkyl, pyridylthio(1-3C)alkyl, styryl, 1-methylimidazol-2-ylthio(1-3C)alkyl, aryl (which may bear one or more halo, hydroxy, (1-4C)alkoxy or (1-4C)alkyl substituents), heteroaryl (which may bear one or more halo, hydroxy, (1-4C)alkoxy or (1-4C)alkyl substituents), or (when $R^4$ is $—COR^5$) α-hydroxybenzyl;

n is 0, 1, 2 or 3;

p is 1 or 2, and when p is 2, n is 1 and $J^2$ is two hydrogens;

$J^2$ is oxygen or two hydrogens;

$L^1$ is carbonyl or methylene;

r is 0, 1, 2, or 3; and $R^6$ is phenyl which may bear one or more halo, trifluoromethyl, (1-4C)alkyl, hydroxy or (1-4C)alkoxy substituents (and particularly one or more chloro or fluoro substituents); naphthyl which may bear one or more halo, trifluoromethyl, (1-4C)alkyl or hydroxy substituents; pyridyl; thienyl; indolyl; quinolinyl; benzothienyl or imidazolyl; or when $L^1$ is carbonyl, the group $—(CH_2)_r—R^6$ may represent aryl, heteroaryl or a benzyl group bearing an α-substituent selected from hydroxy, (1-4C)alkoxy and (1-4)alkyl, and further wherein the aryl, heteroaryl or phenyl portion of the benzyl group may bear one or more substituents selected independently from halo, trifluoromethyl, (1-4C)alkyl, hydroxy and (1-4C)alkyl, hydroxy and (1-4C)alkoxy (and particularly one or more chloro or fluoro substituents); and provided that the compound is not one in which J is oxygen, $R^1$ is phenyl or substituted phenyl or $R^1$ is pyridyl, and $R^2$ is (1-6C)alkyl;

or the N-oxide of the piperidino nitrogen indicated by Δ;

or a pharmaceutically acceptable salt thereof;

or a quaternary ammonium salt thereof in which the piperidino nitrogen indicated by Δ is a quadricovalent ammonium. nitrogen wherein the fourth radical on the nitrogen $R^9$ is (1-4C)alkyl or benzyl and the associated counterion A is a pharmaceutically acceptable anion.

A subgroup of the invention is a compound of formula Ic; or the N-oxide of the piperidino nitrogen indicated by Δ; or a pharmaceutically acceptable salt thereof; or a quaternary ammonium salt thereof;

wherein J, $R^1$, $R^2$, Q, $R^9$ and A have any of the values defined above for a compound of formula I.

It will be appreciated that a compound of formula I (or Ic) contains one or more asymmetically substituted carbon atoms such that such a compound may be isolated in optically active, racemic and/or diastereomeric forms. A compound may exhibit polymorphism. It is to be understood that the present invention encompasses any racemic, optically-active, diastereomeric, polymorphic or stereoisomeric form, or mixture thereof, which form possesses NK2 antagonist properties, it being well known in the art boy to prepare optically-active forms (for example, by resolution of the racemic form or by synthesis from optically-active starting materials) and boy to determine the NK2 antagonist properties by the standard tests described hereinafter may be preferred to use the compound of formula I (or Ic) in a form which is characterized as containing, for example, at least 95%, 98% or 99% enantiomeric excess of the form which is of the (S)-configuration at the center indicated by * in formula Ia, Ib or Ic.

In this specification $R^a$, $R^b$, $R^1$, $R^2$, et cetera stand for generic radicals and have no other significance. It is to be understood that the generic term "(1-6C)alkyl" includes both straight and branched chain alkyl radicals but references to individual alkyl radicals such as "propyl" embrace only the straight chain ("normal") radical, branched chain isomers such as "isopropyl" being referred to specifically. A similar convention applies to other generic groups, for example, alkoxy, alkanoyl, et cetera. Halo is fluoro, chloro, bromo or iodo. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five ring atoms consisting of carbon and one to four heteroatonms selected from oxygen, sulfur and nitrogen or containing six ring atoms consisting of carbon and one or two nitrogens, as well as a radical an ortho-fused bicyclic heterocycle of about eight to ten atoms derived therefrom, particularly a benz-derivative or one derived by fusing a propenylene, trimethylene of tetramethylene diradical thereto, as well as a stable N-oxide thereof.

A pharmaceutically acceptable salt is one made with an acid which provides a physiologically acceptable anion.

Particular values are listed below for radicals, substituents and ranges for a compound of formula I or formula Ic as described above for illustration only and they do not exclude other defined values or other values within defined ranges for the radicals and substituents.

A particular value for J is, for example, oxygen, sulfur, imino, methylimino or ethylimino; and, more particularly, oxygen or sulfur.

A particular value for $R^1$ is, for example, hydrogen, methyl, ethyl, propyl, isopropyl, butyl, hexyl, allyl or cyclohexyl; and a particular value for $R^2$ is, for example, hydrogen, methyl, trifluoromethyl, ethyl, propyl, isopropyl, methylamino or dimethylamino; or a particular value for $R^1$ and $R^2$ together as a group L is trimethylene, tetramethylene or cis-butenylene.

A particular value for m is 2.

When M is formula Ia, a particular value for $Q^a$ is hydrogen, a particular value for $R^3$ is methyl and a particular value for $R^4$ is $—COR^5$. A particular value for $R^5$ is aryl, and more particularly phenyl, which aryl (or phenyl) may bear one or two chloro or fluoro substituents.

When M is formula Ib, a particular value for n is 1 or 2; a particular value for p is 1; a particular value for $J^2$ is two hydrogens; a particular value for $L^1$ is carbonyl; a particular value for r is 0 or 1; and a particular value for $R^6$ is phenyl which may bear one or two halo or (1-4C)alkoxy substituents, and more particularly a chloro, fluoro or isopropoxy substituent.

A particular value for Q is, for example, phenyl which may bear one or two substituents selected from halo, trifluoromethyl and methylenedioxy; and, more particularly, 3,4-dichlorophenyl or 3,4-methylenedioxyphenyl.

A particular value for $R^9$ is methyl or benzyl and for A is, for example, chloride, bromide or methanesulfonate.

A particular subgroup of the invention is a compound of formula Ic wherein

J is oxygen, sulfur or $NR^n$ in which $R^n$ is hydrogen or (1-3C)alkyl;

$R^1$ is hydrogen, (1-6C)alkyl, 2-hydroxyethyl, (3-7C)cycloalkyl, phenyl or a 6-membered heteroaryl containing one or two nitrogens as the heteroatom(s) in which the phenyl or heteroaryl group may bear one or more substituents independently selected from halo, trifluoromethyl, (1-4C)alkyl, (1-4C)alkoxy, nitro, amino and hydroxy;

$R^2$ is hydrogen, (1-6C)alkyl which may bear a hydroxy substituent and/or one to three fluoro substituents, (3-6C)cycloalkyl, (1-5C)alkoxy (only when J is oxygen), (3-6C)cycloalkyloxy (only when J is oxygen), or an amino group of formula $NR^aR^b$ containing zero to about seven carbon atoms in which each of $R^a$ and $R^b$ is independently hydrogen, (1-5C)alkyl or (3-6C)cycloalkyl, or $R^a$ and $R^b$ together with the nitrogen to which they are attached form a pyrrolidino, piperidino, morpholino, thiomorpholino (or its S-oxide) or piperazinyl group (which piperazinyl group may bear a methyl or ethyl group at the 4-position); or $R^1$ and $R^2$ together form a divalent hydrocarbon group L in which the 1-position is bound to the carbon bearing the group J, the divalent group L being selected from trimethylene, cis-propenylene, tetramethylene, cis-butenylene, cis-but-3-enylene, cis,cis-butadienylene, pentamethylene and cis-pentenylene which divalent group L itself may bear one or two methyl substituents; and Q is phenyl which may bear one or two substituents independently selected from halo, trifluoromethyl, hydroxy, (1-3C)alkoxy, (1-3C)alkyl and methylenedioxy; or Q is thienyl, imidazolyl, benzo[b]thiophenyl or naphthyl any of which may bear a halo substituent; or Q is biphenylyl; or Q is carbon-linked indolyl which may bear a benzyl substituent at the 1-position; and provided that the compound is not one in which J is oxygen, $R^1$ is phenyl or substituted phenyl or $R^1$ is pyridyl, and $R^2$ is (1-6C)alkyl;

or a pharmaceutically acceptable salt thereof.

Within that particular subgroup, a particular value for J is one of the particular values describe above for J and a particular value for Q is one of the particular values described above for Q.

One particular group of compounds of formula I or formula Ic is one in which $R^1$ and $R^2$ together form a divalent hydrocarbon group L as defined above and the other radicals and substituents have any of the values defined above. Within that particular group, a particular value for the divalent hydrocarbon radical L formed by $R^1$ and $R^2$ is, for example, trimethylene, cis-propenylene, tetramethylene or cis,cis-butadienylene; and a more particular value is, for example, trimethylene or tetramethylene.

A further particular group of compounds of formula I or formula Ic is one in which J is oxygen;

Q is 3,4-dichlorophenyl;

$R^1$ is hydrogen, (1-6C)alkyl, 2-hydroxyethyl, (3-7C)cycloalkyl, phenyl or a 6-membered heteroaryl containing one or two nitrogens as the heteroatom(s) in which the phenyl or heteroaryl group may bear one or more substituents independently selected from halo, trifluoromethyl, (1-4C)alkyl, (1-4C)alkoxy, nitro, amino and hydroxy; and $R^2$ is hydrogen, (1-6C)alkyl which may bear a hydroxy substituent and/or one to three fluoro substituents, (3-6C)cycloalkyl, (1-5C)alkoxy, (3-6C)cycloalkyloxy or an amino group of formula $NR^aR^b$ containing zero to about seven carbon atoms in which each of $R^a$ and $R^b$ is independently hydrogen, (1-5C)alkyl or (3-6C)cycloalkyl, or $R^a$ and $R^b$ together with the nitrogen to which they are attached form a pyrrolidino, piperidino, morpholino, thiomorpholino (or its S-oxide) or piperazinyl group (which piperazinyl group may bear a methyl or ethyl group at the 4-position); or $R^1$ and $R^2$ together form a 1,3-propanediyl (i.e. trimethylene) group which itself may bear one or two methyl substituents; and provided that the compound is not one in which J is oxygen, $R^1$ is phenyl or substituted phenyl or $R^1$ is pyridyl, and $R^2$ is (1-6C)alkyl;

or a pharmaceutically acceptable salt thereof.

Within that further particular group, a particular value for $R^1$ is, for example, hydrogen, methyl, ethyl, propyl, isopropyl, butyl, hexyl, cyclopentyl, cyclohexyl or phenyl. A particular value for $R^2$ is, for example, methyl, tert-butoxy or methylamino.

Specific compounds of formula I (and of formula Ic) are described in the accompanying Examples; of these, N-[2-(3,4-dichlorophenyl)- 4-[4-(2-oxopyrrolidin-1-yl)piperidino]butyl]-N-methylbenzamide, N-[2-(3,4-dichlorophenyl)-4-[4-(2-oxopiperidino)piperidino]-butyl]-N-methylbenzamide; N-[2-(3,4-dichlorophenyl)-4-[4-(2-thioxopiperidino)piperidino]butyl]-N-methylbenzamide; and N-[2-(3,4-dichlorophenyl)-4-[4-(2-oxo-1,2,5,6-tetrahydropyrid-1-yl)-piperidino]butyl]-N-methylbenzamide; or a pharmacologically acceptable salt thereof, in either the racemic form or as the (S)-enantiomer, are of particular interest.

Pharmaceutically acceptable salts of a compound of formula I (or of formula Ic) include those made with a strong inorganic or organic acid which affords a physiologically acceptable anion, such as, for example, hydrochloric, sulfuric, phosphoric, methanesulfonic, or para-toluenesulfonic acid.

A compound of formula I (or of formula Ic) may be made by processes which include processes known in the chemical art for the production of structurally analogous heterocyclic compounds. Such processes and intermediates for the manufacture of a compound of formula I (or of formula Ic) as defined above are provided as further features of the invention and are illustrated by the following procedures in which the meanings of generic radicals are as defined above unless otherwise indicated:

(a) For a compound of formula I (or of formula Ic), except one in which $R^1$ and $R^2$ together form a divalent hydrocarbon group L, acylating a compound of formula II (or of formula IIc). For a compound of formula I in which J is oxygen, the acylation may be carried out using an acid of formula $R^2COOH$, or an activated derivative thereof, including an isocyanate of formula $R^aNCO$ or $R^bNCO$ for a compound of formula I in which $R^2$ is $NR^aR^b$ and $R^b$ or $R^a$, respectively, is hydrogen. Activated derivatives of an acid of formula $R^2COOH$ include, for example, the corresponding anhydride and the corresponding acid chloride, including the carbamoyl chloride when $R^2$ is $NR^aR^b$ and neither of $R^a$ and $R^b$ is hydrogen. Conveniently, the acylation is carried out at or near room temperature in an inert solvent, for example dichloromethane or tetrahydrofuran, and in the presence of an additional base, for example triethyl amine, for example as described in Example 1. For a compound of formula I in which J is sulfur, the acylation may be carried out using a dithioic acid of formula $R^2CSSH$, or an activated derivative thereof, including an isothiocyanate of formula $R^aNCS$ or $R^bNCS$ for a compound of formula I in which $R^2$ is $NR^aR^b$ and $R^b$ or $R^a$, respectively, is hydrogen. Activated derivatives of an acid of formula $R^2CSSH$ include, for example, the methyl ester. For a compound of formula I in which J is $NR^n$, the acylation may be carried out by using an activated derivative of an imidic acid of formula $R^2C(NR^n)OH$ or a thioimidic acid of formula $R^2C(NR^n)SH$; or, when $R^n$ is hydrogen, using a nitrile of formula $R^2CN$; or, when $R^2$ is $NR^aR^b$, using an activated derivative of the corresponding isourea of formula $R^aR^bNC(NR^n)OH$ or isothiourea of formula $R^aR^bNC(N^RN)SH$ (including a carbodiimide of formula $R^aNCNR^n$ or $R^bNCNR^n$ for a compound of formula I in which $R^2$ is $NR^aR^b$ and $R^b$ or $R^a$, respectively, is hydrogen). An activated derivative of an imidic acid of formula $R^2C(NR^n)OH$ or an isourea of formula $R^aR^bNC-(MR^n)OH$ includes, for example the corresponding imino chloride or the corresponding O-methyl derivative. An activated derivation of a thioimidic acid of formula $R^2C(HR^n)SH$ or an isothiourea of formula $R^aR^bNC(N-R^n)SH$ includes, for example, the corresponding S-methyl derivative.

(b) For a compound of formula I (or of formula Ic) in which J is oxygen and $R^1$ is not hydrogen, phenyl or heteroaryl, except one in which $R^1$ and $R^2$ together form a divalent hydrocarbon group L, alkylating a corresponding compound of formula I (or of formula Ic) in which $R^1$ is hydrogen with a corresponding alkylating agent of formula $R^1X$ in which X is a leaving group and $R^1$ is not hydrogen. Typical values for a leaving group X include, for example, iodide, bromide, methanesulfonate, p-toluenesulfonate, trifluoromethanesulfonate, and the like. It will be clear to one skilled in the art that $R^1X$ includes difunctional alkylating agents such as, for example, dimethyl sulfate. The alkylation is conveniently carried out at or near room termperature in an inert solvent such as for example dimethylformamide or tetrahydrofuran by first deprotonating the compound of formula I in which $R^1$ is hydrogen with a strong base, for example with sodium hydride, followed by treatment with the alkylating agent of formula $R^1X$, for example as described in Example 2. This procedure is generally not preferred if $R^1$ is not a primary alkyl group.

(c) Alkylating a piperidine of formula III with an aldehyde of formula IV (or of formula IVc), by reductive alkylation, or with an alkylating agent of formula V (or of formula Vc) in which Y is a leaving group. Typical values for Y include those listed above for X. The alkylation is preferably carried out by a conventional reductive alkylation, for example as described in Example 6, by the in situ, acid-catalyzed formation of an imminum salt, followed by reduction with sodium cyanoborohydride in alcoholic solvent.

(d) For an N-oxide of the piperidino nitrogen indicated by Δ of a compound of formula I (or of formula Ic), oxidizing the piperidino nitrogen indicated by Δ of a compound of formula I using a conventional procedure, such as, for example, using hydrogen peroxide in methanol, peracetic acid, 3-chloroperoxybenzoic acid in an inert solvent (such as dichloromethane) or dioxirane in acetone.

(e) For a quaternary ammonium salt of a compound of formula I (or of formula Ic), alkylating the piperidino nitrogen indicated by Δ of the compound of formula I (or of formula Ic) with an alkylating agent of formula $R^9Y$ or alkylating a piperidine of formula IIIa with an alkylating agent of formula V, wherein Y is a leaving group, followed, if required, by exchanging the counterion Y for a different counterion A by a conventional method. Typical values for Y include those listed above for X. Exchange of counterions may conveniently be carried out using a basic ion exchange resin in the "A" form.

It may be desired to optionally use a protecting group during all or portions of the above described processes; the protecting group then may be removed when the final compound is to be formed.

Whereafter, for any of the above procedures, when a pharmaceutically acceptable salt of a compound of formula I is required, it may be obtained by reacting the compound of formula I with an acid affording a physiologically acceptable counterion or by any other conventional procedure.

It will also be appreciated that certain of the various optional substituents in the compounds of the invention may be introduced by standard aromatic substitution reactions or generated by conventional functional group modifications either prior to or immediately following the processes above, and as such are included in the process aspect of the invention. Such reactions and modifications include, for example, introduction of nitro or halogeno and reduction of nitro. The reagents and reaction conditions for such procedures are well known in the chemical art.

If not commercially available, the necessary starting materials for the above procedures may be made by procedures which are selected from standard techniques of heterocyclic chemistry, techniques which are analogous to the synthesis of known, structurally similar compounds (particularly those described in the above noted EPA publications and their counterparts), and techniques which are analogous to the above described procedures or the procedures described in the Examples. The starting materials and the procedures for their preparation are additional aspects of the invention.

A convenient intermediate for preparation of starting materials of formulae II, IV, and V (or formula IIc, IVc and Vc) is an alcohol of formula VI (or formula VIc). The preparation of an alcohol of formula VIc in which Q is 3,4-dichlorophenyl is described in Example 1, parts a)–f); and the preparation of the corresponding optically-active alcohol is described in Example 9, parts a)–e). An alcohol of formula VI (or formula VIc) may then be oxidized to the aldehyde of formula IV (or formula IVc), for example using oxalyl chloride, dimethyl sulfoxide and triethylamine as described in Example 1.g) or using Dess-Martin periodinane (1,1,1-triacetoxy-1,1-dihydro-1,2-benziodoxol-3(1H)-one) as described in Example 9.f); or it may be converted into an alkylating agent of formula V (or formula Vc) by a conventional procedure. An aldehyde of formula IV (or formula IVc) may be converted into the corresponding amine of formula II (or formula IIc) in which $R^1$ is hydrogen employing a procedure similar to that described in Example 1, parts h)–i). Using a procedure similar to that described in Example 4.a), an aldehyde of formula IV (or formula IVc) may be converted into a piperidone of formula VII (or formula VIIc); and an amine of formula II may be obtained by reductive alkylation of an amine of formula $R^1NH_2$ using the piperidone of formula VII (or formula VIIc), for example as described in Example 4.b).

For the preparation of a starting material piperidine of formula III, a 1-protected 4-piperidone, prepared for example as described in Example 6, parts a)–c), may be used for a reductive alkylation analogous to that described for a piperidone of formula VII, followed by an acylation similar to that described above in procedure (a), and finally deprotection, for example as described in Example 6, parts d)–e). An analogous method may be used for the preparation of a starting material piperidine of formula III in which $R^1$ and $R^2$ together form a divalent hydrocarbon group L by carrying out the reductive alkylation employing the 1-protected 4-piperidone and a corresponding ω-amino acid, followed by intramolecular cyclization of the resulting amine (for example, analogously to Example 1 of U.S. Pat. No. 4,472,547).

For the preparation of a starting material piperidine of formula III in which $R^1$ and $R^2$ together form a divalent hydrocarbon group L, a 1-protected 4-aminopiperidine, prepared for example as described in Example 7, parts a)–b), may be acylated with an ω-halo acyl halide, for example as described in Example 7.c). Lactam formation by intramolecular-alkylation and finally deprotection, for example as described in Example 7, parts d)–e), conveniently provides a compound of formula III in which J is oxygen and $R^1$ and $R^2$ together form a polymethylene group. For a corresponding compound with a double bond adjacent to the carbonyl group, the double bond may be introduced using a conventional method into the lactam formed upon cyclization before the piperidine nitrogen is deprotected, for example as described in Example 21, parts a)–b). Deprotection of the piperidine nitrogen then affords a compound of formula III in which J is oxygen and $R^1$ and $R^2$ together form a divalent hydrocarbon group with a double bond adjacent to the carbonyl group, for example as described in Example 21.c). For preparation of a compound of formula III in which J is oxygen and $R^1$ and $R^2$ together form cis-but-3-enylene, the 1-protected 4-aminopiperidine may be converted into the corresponding 1-protected 4-(2,6-dioxopiperidino)piperidine by diacylation with an activated glutaric acid derivative, such as the anhydride. Partial reduction of the glutarimide to afford the corresponding 1-protected 4-(2-hydroxy-6-oxopiperidino)piperidine, acid catalyzed dehydration (such as by heating a toluene solution with pare-toluene sulfonic acid) and finally deprotection of the piperidine nitrogen affords a compound of formula III in which J is oxygen and $R^1$ and $R^2$ together form cis-but-3-enylene. A compound of formula III in which J is oxygen and $R^1$ and $R^2$ together form cis,cis-butadienylene may be prepared by dehydrogenation of a compound of formula III in which $R^1$ and $R^2$ form cis-butenylene or, preferably, cis-but-3-enylene with a conventional reagent, such as for example 2,3-dichloro-5,6-dicyano- 1,4-benzoquinone, either before or after deprotection of the piperidino nitrogen. As an alternative to a 1-protected 4-aminopiperidine, 4-aminopyridine may be used to prepare a starting material piperidine of formula III by first substituting the amino group using a similar method to one described above, then hydrogenating the pyridine ring to afford a piperidine of formula III.

When a compound of formula III is required in which J is sulfur, it conveniently may be obtained from a corresponding 1-protected piperidine intermediate in which J is oxygen by treatment with phosphorous pentasulfide or with Lawesson's reagent, 2,4-bis(4-methoxyphenyl)-1,3-dithia-2,4-diphosphetane-2,4-disulfide, followed by deprotection of the piperidine nitrogen, for example as described in Example 9, parts g)–h).

A compound of formula III in which J is $NR^n$ and $R^1$ and $R^2$ together form a divalent hydrocarbon group generally may be obtained from one of the above described 1-protected piperidine lactam derivatives by conversion using a conventional method of the lactam carbonyl group to the iminium chloride or the vinyl chloride, or a corresponding methoxy or methyl thio derivative, followed by treatment with an amine of formula $H_2NR^n$, and finally deprotection of the piperidine nitrogen. In addition, a compound of formula III in which J is NH and $R^1$ and $R^2$ together form a divalent hydrocarbon group (or the corresponding 1-protected derivative) may be obtained by the intramolecular cyclization of the corresponding nitrile using trimethyl aluminum to effect the cyclization. When $R^1$ and $R^2$ form a polymethylene group, a diprotected 4-aminopiperidine derivative, such as the 4-tert-butoxycarbonylaminopiperidine derivative described at Example 7.a), may be alkylated on the amino nitrogen with the requisite ω-halo nitrile, then the amino protecting group removed using a conventional acidic reagent such as hydrogen chloride, to afford the salt of the amino nitrile to be cyclized. When a double bond is required in the divalent hydrocarbon radical, the nitrile may be prepared stepwise in a conventional manner to introduce the double bond, for example as described in European Patent Application, Publication Number 529655 and illustrated therein in Reaction Scheme 3.

A starting material piperidine of formula IIIa may be obtained from a piperidine of formula III by reductive alkylation to introduce the substutient $R^9$, or the compound may be prepared in a manner analogous to the preparation of a piperidine of formula III.

As will be clear to one skilled in the art, a variety of sequences is available for preparation of the starting materials, and the sequences leading to the starting materials and products of the invention may be altered if appropriate considerations regarding the synthetic methods and radicals present are followed.

The utility of a compound of the invention or a pharmaceutically acceptable salt thereof (hereinafter, collectively referred to as a "Compound") may be demonstrated by standard tests and clinical studies, including those disclosed in the EPA publications noted above, such as EPA 428434 or EPA 474561 (or U.S. Pat. No. 5,236,921), and those described below.

Neurokinin A (NKA) Receptor-binding Assay (Test A)

The ability of a Compound of the invention to antagonize the binding of NKA at the NK2 receptor may be demonstrated using an assay using the human NK2 receptor expressed in Mouse Erythroleukemia (MEL) cells by using MEL cell membranes (MELM) which bear high-affinity and selective NK2 receptors and which is carried out as follows.

MEL CELL EXPRESSION OF HUMAN NK2 RECEPTOR (hNK2R)

Figure 1:
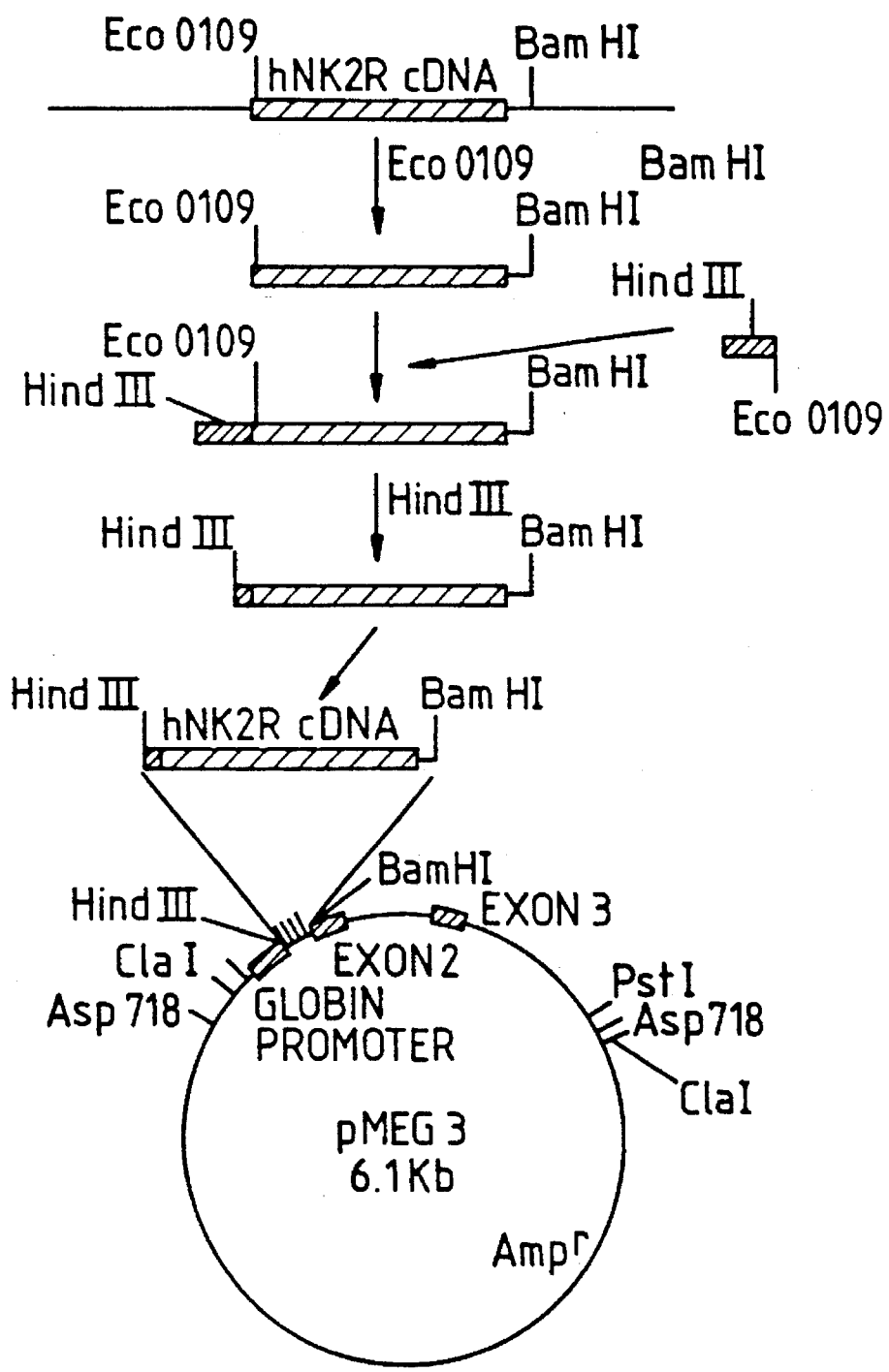
FIG. 1 shows construction of the MEL cell expression vector construct pMEG3/hNK2R.
Figure 2:
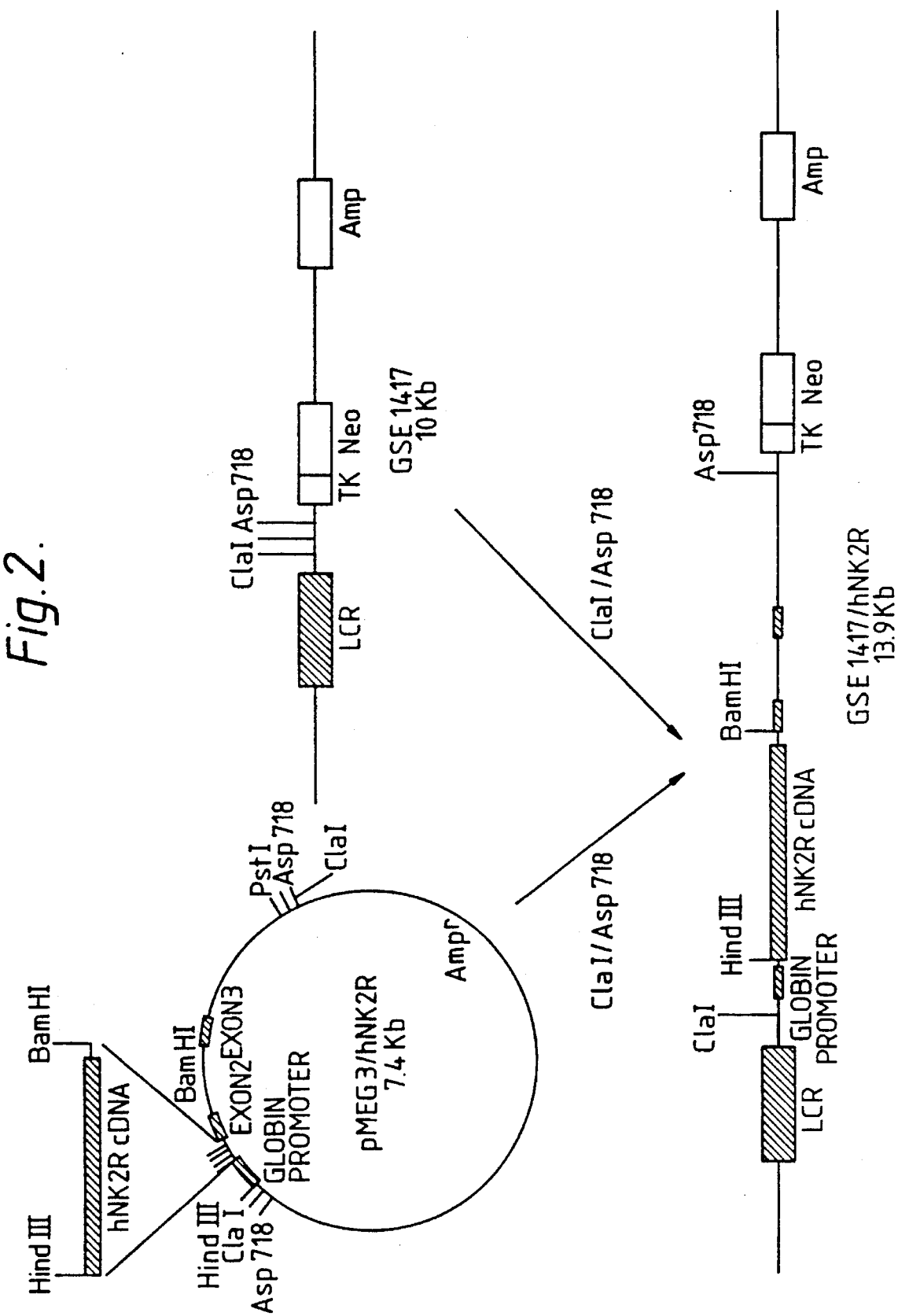
FIG. 2 shows construction of the expression vector construct GSE1417/hNK2R.
Figure 3:
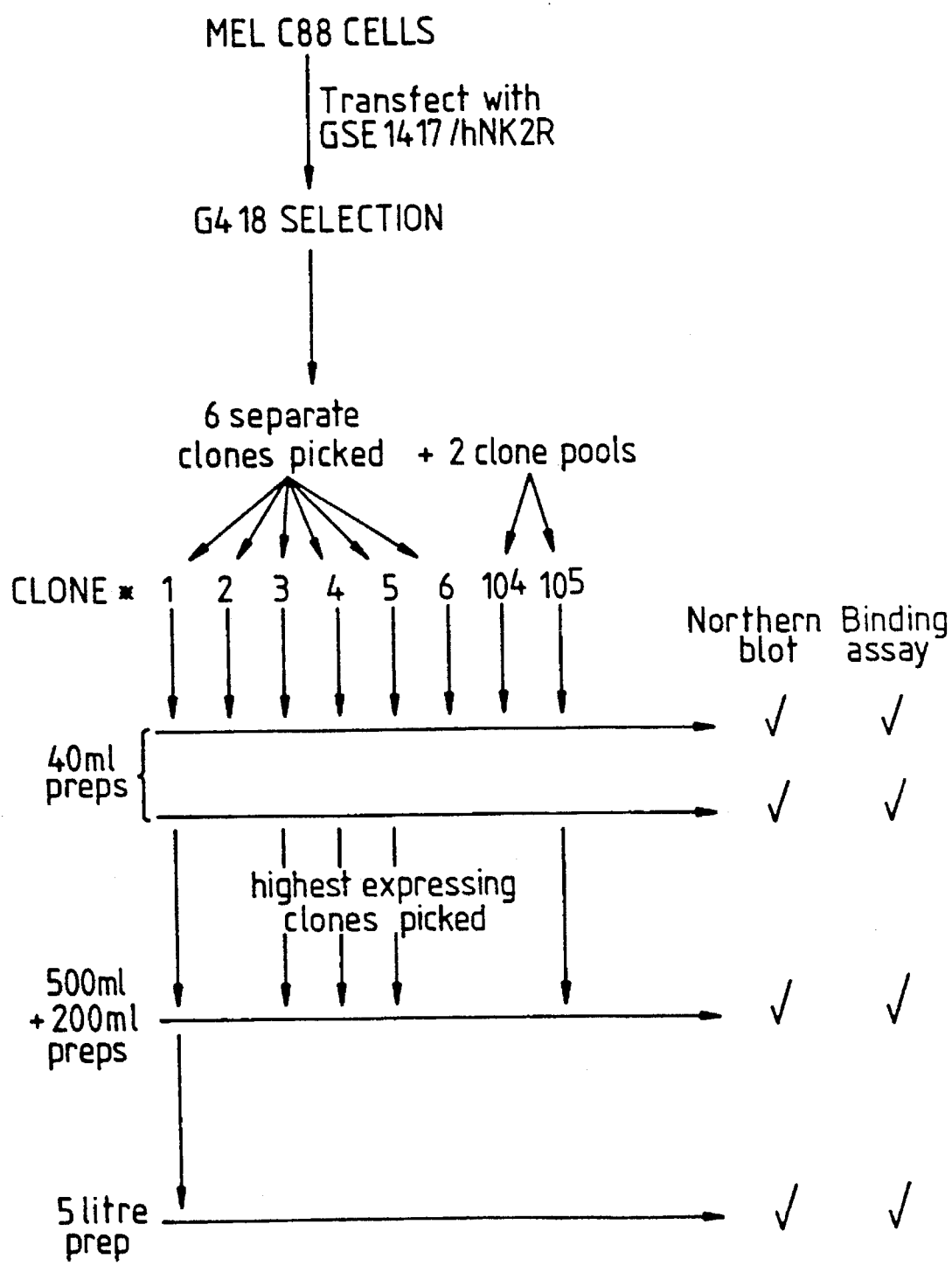
FIG. 3 shows expression of human NK2 receptor in MEL C88 cells.

Heterologous protein expression in Mouse Erythroleukemia (MEL) cells uses the human globin locus control region (LCR) (F. Grosveld et al., *Cell* (1987) 51, 975–985). The cDNAs are inserted between the human beta-globin promoter and the second intron of the human beta-globin gene, and this expression cassette is then placed downstream of the LCR and transfected into MEL cells (M. Needham et al., *Nucl. Acids Res.* (1992) 20, 997–1003). Human NK2 receptor cDNA (A. Graham et al., *Biochem. Biophys. Res. Commun.* (1991) 177, 8–16) was isolated from human lung RNA by polymerase chain reaction and DNA sequenced. Human NK2 receptor cDNA was subcloned into a shuttle vector (pMEG3) containing the beta-globin promoter and the 3' portion of the human beta-globin gene (FIG. 1). Human NK2 receptor cDNA was restricted with Eco 0109 (5' end) and Bam HI (3' end). An oligonucleotide linker-adaptor containing an internal Hind III site and a 3' end Eco 0109 site was ligated to the hNK2R cDNA fragment. The sequence of the top strand oligonucleotide=5'd(GCGCAAGCT-TATGGG) (SEQ ID NO:1) and the bottom strand oligonucleotide=5'd(GTCCCCATAAGCTTGCGC) (SEQ ID NO:2). These were annealed and ligated to the hNK2R fragment by standard methods. Following cleavage with Hind III, the resulting fragment was cloned into the Hind III and Bam HI sites in the polylinker of the shuttle vector pMEG3. The construct (pMEG3/hNK2R) was verified by restriction mapping and sequencing the 5' end and 3' end junctions of cDNA/vector. This was then transformed into E.coli DH5 alpha, and plasmid DNA was isolated by standard methods and verified by restriction mapping and DNA sequencing. A ClaI/Asp718 cassette carrying the beta-globin promoter, human NK2 receptor cDNA and the 3' beta-globin Eerie fragment was excised and subcloned downstream of the LCR in plasmid pGSE1417 (FIG. 2). The pMEG3/hKNK-2R construct was cleaved with ClaI and Asp718 and cloned directly into the ClaI and Asp718 sites (3' of LCR) in the expression vector GSE1417. The construct GSE1417/hNK2R (13.9 kb) was verified by restriction mapping. E.coli DH5 alpha was transformed and recombinant plasmids verified by restriction mapping. MEL C88 cells (A. Deisseroth et al., *Cell* (1978) 15, 55–63) were electroporated (M. Antoniou, *Methods Molecular Biology* (1991) 7, 421–434) with PvuI linearized pGSE1417/human NK2 receptor DNA. Directly after transfection, cells were diluted in culture medium to $10^4$ and $10^5$ cell per mL and 1 mL aliquots transferred to each well of a 24-well plate. G418 was added to a concentration of 1 mg/mL 24 hours after the transfection to select for stable transfectants. Individual clones were picked or pooled to generate populations seven to ten days after the addition of selective medium. FIG. 3 shows the strategy used to isolate transfected MEL/human NK2 receptor cell line. For expression studies, cells were maintained in exponential growth for a period of four days, and then dimethyl sulfoxide (DMSO) was added to a final concentration of 2% (v/v) to induce differentiation and hence expression. Samples were taken 4 days post induction for mKNA and NKA binding analyses. The results indicated that clone #1 expresses hNK2R at the highest level (both hNK2R mRNA and specific NKA binding). This clone was scaled up and is now routinely fermented at 20 liter scale per month and supplied for use in Test A.

Membrane preparations (MELM) prepared from the MEL cells containing high-affinity NK2 receptors were prepared according to a published protocol (D. Aharony, et al., *Neuropeptides* (1992) 23, 121–130) with the following minor modifications: (1) Iodoacetamide (1 mM) was included in the homogenization buffer; (2) Homogenization was as published but for a shorter period of 10 seconds once and at a slower speed (setting 10); and (3) The equilibration step with KCl/EDTA was not performed. In a typical preparation, binding of $^3$H-NKA (2.5 nM) to MELM was highly specific (88±4%) and linearly dependent on the protein concentration, with significant binding detected as low as 26 μg protein/mL. Equilibrium-competion experiments demonstated binding to high-affinity, high-density receptors with $K_D$=1187 nM, $B_{max}$2229 fmol/mg protein.

The radio ligand $^3$H-neurokinin A ($^3$H-NKA) as [4,5-$^3$H-Leu$^9$]-NKA (typical specific activity, 117 Ci/mmol) is obtained by custom synthesis from Cambridge Research Biochemicals and is >95% pure. Repeated HPLC analysis demonstrated that the ligand is stable under proper storage conditions (silanized vials with 0.2% mercaptoethanol, under argon). Also, no degradation or metabolism is apparent in the receptor-binding assay.

The assay is carried out using an incubation buffer consisting of 50 mM Tris HCl (pH 7.4), 5 mM Mg$^{++}$, 100 μM thiorphan, 1 nM $^3$H-NKA, 0.02% (w:v) BSA, 30 mM K$^+$, and 300 μM dithiothreitol; and the concentration of membrane protein is held at approximately 0.05–0.025 mg per tube. Nonspecific binding is routinely defined with 1 μM NKA. Each tube receives the following: 150 μL incubation buffer, 20 μL $^3$H-NKA 20 μL Compound, NKA or buffer as appropriate, and 125 μL membrane suspension. The reaction is initiated by the addition of the membranes. The tubes are incubated for 60 min at 25° C. in a shaking water bath. The reaction is terminated by washing the tubes with 10 mL of ice-cold 50 mM Tris HCl using a Brandel cell harvesting system using Whatman GF/B filters which have been soaked at least 4 hours at room temperature in 0.01% (w:v) polyethylenimine to collect the membranes. The filters are deposited in scintillation vials and read in a Beckman LS 6000LL Scintillation Counter. The binding constant $K_i$ is calculated by standard methods and is typically the mean of several such determinations. The $K_i$ values may be converted to negative logarithms and expressed as -log molar $K_i$ (i.e. $pK_i$).

In an initial use of this assay, the $IC_{50}$ measured for the standard compound L-659,877 was found to be 30 nM versus $^3$H-NKA binding to MELM. The selectivity of a Compound for binding at the NK2 receptor may be shown by determining its binding at other receptors using standard assays, for example, one using a tritiated derivative of SP in a tissue preparation selective for NK1 receptors or one using a tritiated derivative of NKB in a tissue preparation selective for NK3 receptors.

Guinea Pig Assay (Test B)

In the test described below either NKA or [β-ala$^8$]-NKA(4-10) is used as an agonist. The chosen agonist is refered to as AG throughout the description. The ability of a Compound of the invention to antagonize the action of AG in a pulmonary tissue may be demonstrated using a functional assay in guinea pig trachea, which is carried out as follows.

Male guinea pigs are killed by a sharp blow to the back of the head. The trachea are removed, trimmed of excess tissue and divided into two segments. Each segment is suspended as a ring between stainless steel stirrups in water-jacketed (37.5° C.) tissue baths containing a physiological salt solution of the following composition (mM): NaCl, 119; KCl 4.6; CaCl$_2$, 1.8; MgCl$_2$, 0.5; NaH$_2$PO$_4$, 1; NaHCO$_3$, 25; glucose, 11; thiorphan, 0.001; and indomethacin, 0.005; gassed continuously with 95% O$_2$-%5 CO$_2$. Initial tension placed on each tissue is 1 g, which is maintained throughout a 0.5 to 1.5 hour equilibration period before addition of other drugs. Contractile responses are measured on a Grass polygraph via Grass FT-03 force transducers.

Tissues are challenged repetitively with a single concentration of AG (10 nM) with intervening 30 min periods with washing to allow the tension to return to baseline levels. The magnitude of the contractions to AG reaches a constant level after two challenges, and each Compound is tested for inhibition of responses to AG by addition to the tissue bath 15 minute before the third or subsequent exposure to the agonist. The contractile response to AG in the presence of Compound is compared to that obtained with the second AG challenge (in the absence of Compound). Percent inhibition is determined when a Compound produces a statistically significant (p<0.05) reduction of the contraction and is calculated using the second contractile response as 100%.

Potencies of selected Compounds are evaluated by calculating apparent dissociation constants ($K_B$) for each concentration tested using the standard equation:

$$K_B=[\text{antagonist}]/(\text{dose ratio}-1)$$

where dose ratio=antilog[(AG -log molar EC$_{50}$ without Compound)—(AG -log molar EC$_{50}$ with Compound)]. The $K_B$ values may be converted to the negative logarithms and expressed as -log molar $K_B$ (i.e. $pK_B$). For this evaluation, complete concentration-response curves for AG are obtained in the absence and presence of Compound (30 min incubation period) using paired tracheal rings. The potency of AG is determined at 50% of its own maximum response level in each curve. The EC$_{50}$ values are converted to the negative logarithms and expressed as -log molar EC$_{50}$. Maximum contractile responses to AG are determined by expressing the maximum response to AG as a percentage of the contraction caused by carbachol (30 μM), added after the initial equilibration period. When a statistically significant (p<0.05) reduction of the maximum response to AG is produced by a compound, the percent inhibition is calculated relative to the percentage of carbachol contraction in the untreated, paired tissue used as 100%.

Clinical studies to demonstrate the efficacy of a Compound of the invention may be carried out using standard methods. For example, the ability of a Compound to prevent or treat the symptoms of asthma or asthma-like conditions may be demonstrated using a challenge of inhaled cold air or allergen and evaluation by standard pulmonary measurements such as, for example, $FEV_1$ (forced expiratory volume in one second) and FVC (forced vital capacity), analyzed by standard methods of statistical analysis.

It will be appreciated that the implications of a Compound's activity in Test A or Test B is not limited to asthma, but rather, that the test provides evidence of general antagonism of NKA. In general, the Compounds of the invention which were tested demonstrated statistically significant activity in Test A with a $K_i$ of 1 μM or much less. For example, the compound described in Example 4 was typically found to have a $K_i$ of 3.5 nM. In Test B, a $pK_B$ of 5 or greater was typically measured for a Compound of the invention. For example, a $pK_B$ of 7.7 was measured for the compound described in Example 4. It should be noted that there may not always be a direct correlation between the activities of Compounds measured as $K_i$ values in Test A and the values measured in other assays, such as the $pK_B$ measured in Test B.

As discussed above, a compound of formula I or a pharmaceutically acceptable salt thereof possesses NKA antagonist properties. Accordingly, it antagonizes at least one of the actions of NKA which are known to include bronchoconstriction, increased microvascular permeability, vasodilation and activation of mast cells. Accordingly, one feature of the invention is the use of a compound of formula I or a pharmaceutically acceptable salt thereof in the treatment of a disease in a human or other mammal in need thereof in which NKA is implicated and antagonism of its action is desired, such as for example the treatment of asthma or a related disorder. In addition, another feature of the invention is provided by the use of a compound of formula I or a salt thereof as a pharmacological standard for the development and standardization of new disease models or assays for use in developing new therapeutic agents for treating the diseases in which NKA is implicated or for assays for their diagnosis.

When used in the treatment of such a disease, a compound of the invention is generally administered as an appropriate pharmaceutical composition which comprises a compound of formula I or a pharmaceutically acceptable salt thereof as defined hereinbefore and a pharmaceutically acceptable diluent or carrier, the composition being adapted for the particular route of administration chosen. Such a composition is provided as a further feature of the invention. It may be obtained employing conventional procedures and excipients and binders, and it may be one of a variety of dosage forms. Such forms include, for example, tablets, capsules, solutions or suspensions for oral administration; suppositories for rectal administration sterile solutions or suspensions for administration by intravenous or intramuscular infusion or injection; aerosols or nebulizer solutions or suspensions for administration by inhalation; or powders together with pharmaceutically acceptable solid diluents such as lactose for administration by insufflation.

For oral administration a tablet or capsule containing up to 250 mg (and typically 5 to 100 mg) of a compound of formula I may conveniently be used. For administration by inhalation, a compound of formula I will be administered to humans in a daily dose range of, for example, 5 to 100 mg, in a single dose or divided into two to four daily doses. Similarly, for intravenous or intramuscular injection or infusion a sterile solution or suspension containing up to 10% w/w (and typically 0.05 to 5% w/w) of a compound of formula I may conveniently be used.

The dose of a compound of formula I to be administered will necessarily be varied according to principles well known in the art taking account of the route of administration and the severity of the condition and the size and age of the patient under treatment. However, in general, the compound of formula I will be administered to a warm-blooded animal (such as man) so that a dose in the range of, for example, 0.01 to 25 mg/kg (and usually 0.1 to 5 mg/kg) is received. It will be understood that generally equivalent amounts of a pharmaceutically acceptable salt of a compound of formula I may be used.

The invention will now be illustrated by the following non-limiting examples in which, unless stated otherwise:

(i) temperatures are given in degrees Celsius (° C.); operations were carried out at room or ambient temperature, that is, at a temperature in the range of 18°–25° C.;

(ii) organic solutions were dried over anhydrous sodium sulfate; evaporation of solvent was carried out using a rotary evaporator under reduced pressure (600–4000 pascals; 4.5–30 mm Hg) with a bath temperature of up to 60° C.;

(iii) chromatography means 'flash chromatography' (method of Still) carried out on Merck Kieselgel (Art 9385 from E. Merck, Darmstadt, Germany); reversed phase silica gel means octadecylsilane (ODS) coated support having a particle diameter of 32–74μ, known as "PREP-40-ODS" (Art 731740-100 from Bodman Chemicals, Aston, Pa., USA); thin layer chromatography (TLC) was carried out on 0.25 mm silica gel GHLF plates (Art 21521 from Artaltech, Newark, Del., USA);

(iv) in general, the course of reactions was followed by TLC and reaction times are given for illustration only;

(v) melting points are uncorrected and (d) indicates decomposition; the melting points given are those obtained for the materials prepared as described; polymorphism may result in isolation of materials with different melting points in some preparations;

(vi) final products had satisfactory nuclear magnetic resonance (NMR) spectra and were substantially pure by TLC;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 300 MHz using $CDCl_3$ as solvent; conventional abbreviations for signal shape are used; for AB spectra the directly observed shifts are reported.

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume: volume (v/v) terms; and (xii) mass spectra (MS) were run with an electron energy of 70 electron volts in the chemical ionizaton mode using a direct exposure probe; generally, only peaks which indicate the parent mass are reported.

EXAMPLE 1

N-[4-(4-Acetamidopiperidino)-2-(3,4-dichlorophenyl)butyl]-N-methylbenzamide

To a solution of N-[4-(4-aminopiperidino)-2-(3,4-dichlorophenyl)butyl]-N-methylbenzamide (1.5 g) in dichloromethane (35 mL) was added triethylamine (0.60 mL) and acetic anhydride (0.41 mL), and the resulting solution was allowed to stir for 30 minutes. The mixture was diluted with dichloromethane and was washed (0.3N sodium hydroxide, water), dried, and evaporated. The material was dissolved in toluene and the resulting solution was evaporated to give the title compound (1.63 g) as a white solid; MS: m/z=476(M+1). Analysis for $C_{25}H_{31}Cl_2N_3O_2 \cdot 0.2\ C_6H_5CH_3$: Calculated: C, 64.07; H, 6.63; N, 8.49; Found: C, 64.04; H, 6.59; N, 8.32.

The intermediate amine was prepared as follows:

a. 1-Bromo-2-(tetrahydropyran-2-yloxy)ethane. To a mechanically stirred solution of dihydropyran (1 L) and a strong acid ion exchange resin (10.0 g) in hexane (2 L) was added 2-bromoethanol (985 g) dropwise over a period of 1.5 hours. Throughout the addition, a cold water bath was used to maintain an internal temperature of 35°–40° C. After being stirred overnight at room temperature, the reaction mixture was chromatographed, eluting with hexane (6 L). The eluent was evaporated to give an amber liquid which was distilled through a 2 inch vigreux column. The material boiling between 75°–95° C. (3,300–4,700 Pa) was collected and redistilled to give the ether (1195.5 g) as an oil; bp 80°–90° C. (2666 Pa); NMR: 4.68 (m,1), 4.01 (m,1), 3.89 (m,1), 3.77 (m,1), 3.52 (m,3), 1.75–1.50 (m,6).

b. 2-(3,4-Dichlorophenyl)-4-(tetrahydropyran-2-yloxy)-butyronitrile. To a solution of sodium hydride (218.0 g of a 55% oil suspension) in tetrahydrofuran (4 L) at 10° C. in an ice/water bath was added 3,4-dichlorophenylacetonitrile (893.0 g) in tetrahydrofuran (2 L) over a period of 45 minutes, and the resulting solution was allowed to stir for 2 hours at room temperature. The mixture was cooled in an ice/water bath and 1-bromo-2-(tetrahydropyran-2-yloxy)ethane (1076.0 g) was dropped in as a neat oil over a period of 25 minutes. The mixture was stirred overnight at room temperature and divided into four 2-liter portions. Each portion was diluted with saturated ammonium chloride (3 L) and extracted with ether (500 mL). The combined organic layers were washed (aqueous ammonium chloride), dried, and evaporated. The resulting material was chromatographed, with hexane:dichloromethane (gradient 100:0, 0:100) as the eluent, to give the nitrile (932 g) as an oil; NMR: 7.47 (m,4), 7.20 (m,2), 4.57 (m,2), 4.08 (m,2), 3.85 (m,4), 3.54 (m,3), 3.37 (m,1), 2.15 (m,4), 1.77 (m,4), 1.56 (m,8).

c. 2-(3,4-Dichlorophenyl)-4-(tetrahydropyran-2-yloxy)butylamine. To a solution of the above nitrile (128.3 g) in 95% ethanol (1.1 L) and concentrated ammonium hydroxide (550 mL) was added Raney Nickel (25.0 g). The mixture was placed under a hydrogen atmosphere (3.6 bar) for 1.5 days. The mixture was filtered through diatomaceous earth to remove the catalyst, and the resulting filtrate was evaporated. The resulting material was chromatographed, with dichloromethane:methanol (gradient 100:0, 95:5) as the eluent, to give the amine (91 g) as an oil; NMR: 7.40 (s,1), 7.38 (s,1), 7.32 (d,1, J=2.1), 7.28 (d,1, J=2.0), 7.07 (dd,1, J=2.1, 4.9), 7.04 (dd,1, J=2.1, 4.9), 4.50 (m,1), 4.43 (m,1), 3.70 (m,4), 3.45 (m,2), 3.27 (m,1), 3.17 (m,1), 2.97–2.75 (m,6), 2.00 (m,2), 1.82–1.66 (m,6), 1.53 (m,8), 1.18 (broad s,4); MS: m/z=318(M+1), 234[(M+1)-tetrahydro-pyranyl].

d. N-[2-(3,4-Dichlorophenyl)-4-(tetrahydropyran-2-yloxy)butyl]-benzamide. To a solution of the above amine (2.5 g) in dichloromethane (35 mL) was added triethylamine (1.1 mL) and benzoic anhydride (1.85 g), and the resulting solution was allowed to stir for 45 minutes. The mixture was washed (0.2N hydrochloric acid, 1N sodium hydroxide, water), dried, and evaporated to give the amide (3.3 g) as an oil; MS: m/z=338[(M+1)-tetrahydropyranyl]; NMR: 7.63 (m,4), 7.46 (m,2), 7.37 (m,8), 7.09 (m,2), 6.22 (m,2), 4.50 (m,1), 4.43 (m,1), 3.8 (m,5), 3.63 (m,1), 3.5 (m,4), 3.36 (m,1), 3.23 (m,1), 3.11 (m,2), 2.06 (m,2), 1.90–1.77 (m,4), 1.68 (m,2), 1.51 (m,8).

e. N-[2-(3,4-Dichlorophenyl)-4-(tetrahydropyran-2-yloxy)butyl]-N-methylbenzamide. To a solution of the above amide (3.3 g) in dimethyl sulfoxide (20 mL) was added powdered potassium hydroxide (1.6 g). After 15 minutes, iodomethane (1.0 mL) was added. After 1 hour, the mixture was diluted with water and extracted with dichloromethane. The combined organic extracts were dried and evaporated to give the N-methyl amide (3.1 g) as an oil; MS: m/z=352 [(M+1)-tetrahydropyranyl].

f. N-[2-(3,4-Dichlorophenyl)-4-hydroxybutyl]-N-methylbenzamide. To a solution of the above N-methyl amide (10.5 g) in tetrahydrofuran (100 mL) was added 6N hydrochloric acid (50 mL), and the resulting solution was allowed to stir overnight. The mixture was neutralized with 10N sodium hydroxide, diluted with water (200 mL), and extracted with dichloromethane. The organic layer was dried and evaporated. The resulting yellow solid was suspended in ether and filtered to give the alcohol (8.4 g) as a white solid; MS: m/z=352(M+1).

g. N-[2-(3,4-Dichlorophenyl)-4-oxobutyl]-N-methylbenzamide. To a solution of oxalyl chloride (2.6 mL) in dichloromethane (60 mL) at −78° C. was added dimethyl sulfoxide (4.2 mL) in dichloromethane (30 mL), followed by the above alcohol (8.3 g) in dimethyl sulfoxide (6 mL) and dichloromethane (30 mL). The resulting solution was allowed to stir for 30 minutes, and triethylamine (16.4 mL) was added. The mixture was allowed to warm to room temperature, diluted with dichloromethane, washed (1N hydrochloric acid, saturated aqueous sodium bicarbonate, water), dried, and evaporated. The resulting yellow solid was suspended in ether and filtered to give the the aldehyde (6.4 g) as a white solid; MS: m/z=350(M+1).

h. N-[4-(4-tert-Butoxycarbonylaminopiperidino)-2-(3,4-dichlorophenyl)butyl]-N-methylbenzamide. To a solution of 4-tert-butoxycarbonylaminopiperidine (5.4 g) in methanol (70 mL) was added acetic acid (1.5 mL) and the above aldehyde (6.3 g) in methanol (30 mL). The resulting solution was allowed to stir for 2 minutes. Sodium cyanoborohydride (1.7 g) in methanol (10 mL) was added, and the mixture was allowed to stir overnight. The mixture was neutralized with saturated aqueous sodium bicarbonate, stirred for 30 minutes, diluted with water, and extracted with dichloromethane. The organic layer was dried and evaporated to give the piperidine (6.7 g) as a white foamy solid; MS: m/z=534(M+1); Analysis for $C_{28}H_{37}Cl_2N_3O_3 \cdot 0.18\ CH_2Cl_2$: Calculated: C, 61.56; H, 6.84; N, 7.64; Found: C, 61.69; H, 6.77; N, 7.63.

i. N-[4-(4-Aminopiperidino)-2-(3,4-dichlorophenyl)butyl]-N-methylbenzamide. To a solution of the above piperidine (1.9 g) in dichloromethane (18 mL) was added trifluoroacetic acid (4.9 mL), and the resulting solution was allowed to stir for 7 hours. The mixture was diluted with dichloromethane, neutralized with 2.2M sodium hydroxide followed by aqueous sodium bicarbonate, and washed with water. The organic extracts were dried and evaporated to give the amine (1.5 g) as a yellow oil; MS: m/z=434(M+1).

The intermediate 4-tert-butoxycarbonylaminopiperidine used in Example 1.h. was prepared as follows:

j. 4-tert-Butoxycarbonylaminopiperidine. To a solution of 1-benzyl-4-aminopiperidine (66.2 g) in tetrahydrofuran (275 mL) was added dropwise di-tert-butyl dicarbonate (76.0 g)

in tetrahydrofuran (50 mL). After being stirred for 4 hours, the mixture was evaporated and redissolved in 95% ethanol (1250 mL) in a 2 L stainless steel (Parr) reactor. 10% Palladium on carbon (13.6 g) in 95% ethanol (100 mL) was added and the mixture was placed under a hydrogen atmosphere (3.44 bars) at 45° C. for 3 hours. The resulting solution was filtered through diatomaceous earth/silica gel and evaporated to give the aminopiperidine (72.5 g) as a white solid; MS: m/z=201(M+1); NMR: 4.61 (m,1), 3.51 (m,1), 3.07 (m,1), 3.03 (m,1), 2.65 (m,2), 1.93 (m,2), 1.58 (m,1), 1.45 (s,9), 1.27 (m,2).

EXAMPLE 2

N-[2-(3,4-Dichlorophenyl)-4-[4-(N-ethylacetamido)-piperidino]butyl]-N-methylbenzamide.

To a flask containing sodium hydride (0.16 g of a 60% oil suspension washed with hexane) was added N-[4-(4-acetamidopiperidino)-2-(3,4-dichlorophenyl)butyl]-N-methylbenzamide (0.40 g) in tetrahydrofuran (1.6 mL), followed by iodoethane (0.34 mL). After being stirred overnight, the mixture was quenched with water and extracted with ether:ethyl acetate (1:1). The combined organic extracts were washed (brine), dried, and evaporated. The resulting material was chromatographed, with dichloromethane:methanol (95:5) as the eluent, to give the title compound as a white solid (0.32 g) after evaporation from ether; MS: m/z= 504(M+1). Analysis for $C_{27}H_{35}Cl_2N_3O_2 \cdot 0.11$ $CH_2Cl_2$: Calculated: C, 63.36; H, 6.91; N, 8.17; Found: C, 63.19; H, 6.94; N, 8.17.

EXAMPLE 3

N-[4-[4-(N-Butylacetamido)piperidino]-2-(3,4-dichlorophenyl)butyl]-N-methylbenzamide hydrochloride.

Using a procedure similar to that described in Example 2, except replacing iodoethane with iodobutane and extracting with dichloromethane instead of ether/ethyl acetate, N-[4-[4-(N-butylacetamido)piperidino]-2-(3,4-dichlorophenyl)butyl]-N-methylbenzamide was prepared. The crude material was dissolved in methanolic hydrogen chloride, and the resulting solution was concentrated to give the title compound; MS: m/z=532(M+1). Analysis for $C_{29}H_{39}Cl_2N_3O_2 \cdot 2.5$ HCl: Calculated: C, 55.84; H, 6.71; N, 6.74; Found: C, 55.71; H, 6.91; N, 6.62.

EXAMPLE 4

N-[4-[4-(N-Cyclohexylacetamido)piperidino]-2-(3,4-dichlorophenyl)butyl]-N-methylbenzamide.

N-[4-(4-cyclohexylaminopiperidino)-2-(3,4-dichlorophenyl)-butyl]-N-methylbenzamide was dissolved in dichloromethane (4.0 mL), and triethylamine (1.0 mL) and acetic anhydride (0.65 mL) were added. After being stirred for 2 hours, the mixture was washed with aqueous sodium bicarbonate, dried, and evaporated. The resulting material was chromatographed, with dichloromethane:methanol (95:5) as the eluent, to give the title compound (0.60 g) as a white solid; MS: m/z=558(M+1). Analysis for $C_{31}H_{41}Cl_2N_3O_2 \cdot 0.6$ $CH_2Cl_2$: Calculated: C, 62.26; H, 6.98; N, 6.89. Found: C, 62.15; H, 6.99; N, 7.30

The intermediate amine was prepared as follows:

a. N-[2-(3,4-Dichlorophenyl)-4-(4-oxopiperidino)butyl]-N-methylbenzamide. To a solution of 1,4-dioxa-8-azaspiro [4.5]decane (1.28 mL) in methanol (5 mL) at 0° C. was added acetic acid (0.57 mL) and the aldehyde described at Example 1.g. (2.8 g) in methanol (20 mL), and the resulting solution was allowed to stir for 10 minutes. Sodium cyanoborohydride (0.67 g) in methanol (5 mL) was added, and the mixture was allowed to stir for 3 days at room temperature. The mixture was diluted with 0.05M sodium hydroxide and extracted with ethyl acetate. The organic extracts were washed (brine), dried, and evaporated. The resulting material was dissolved in trifluoroacetic acid (25 mL), water (2 mL) was added, and the solution was heated at 60° C. for 90 minutes. The mixture was neutralized with dilute aqueous sodium hydroxide and extracted with dichloromethane. The organic extracts were dried and evaporated to give the ketone (2.6 g) as a white foamy solid; MS: m/z=433(M+1).

b. N-[4-(4-Cyclohexylaminopiperidino)-2-(3,4-dichlorophenyl)-butyl]-N-methylbenzamide. To a solution of cyclohexylamine (0.20 mL) in ethanol (1 mL) at 0° C. was added acetic acid (0.10 mL) and the above ketone (0.60 g) in methanol (2 mL). The resulting solution was allowed to stir for 5 minutes and sodium cyanoborohydride (0.11 g) in methanol (2 mL) was added. The mixture was allowed to stir overnight at room temperature and the solvent was evaporated to give the amine.

EXAMPLE 5

N-[2-(3,4-Dichlorophenyl)-4-[4-(N-hexylacetamido)-piperidino]butyl]-N-methylbenzamide hydrochloride.

To N-[2-(3,4-dichlorophenyl)-4-(4-hexylaminopiperidino)-butyl]-N-methylbenzamide in dichloromethane (5 mL) was added triethylamine (0.39 mL) and acetic anhydride (0.39 mL). After being stirred for 2 hours, the mixture was diluted with 1N sodium hydroxide and was extracted with dichloromethane. The combined organic extracts were washed (brine), dried, and evaporated. The resulting material was chromatographed, with dichloromethane:methanol (97:3) as the eluent, to give the title compound (0.210 g) as a white solid after evaporation from methanolic hydrogen chloride; MS: m/z=560(M+1). Analysis for $C_{31}H_{43}Cl_2N_3O_2 \cdot 1.5$ HCl: Calculated: C, 60.51; H, 7.28; N, 6.82; Found: C, 60.50; H, 7.38; N, 6.85.

The intermediate amine was prepared as follows:

a. N-[2-(3,4-Dichlorophenyl)4-(4-hexylaminopiperidino)-butyl]-N-methylbenzamide. To a solution of hexylamine (0.92 mL) in methanol (2 mL) at 0° C. was added acetic acid (0.40 mL) and the ketone described in Example 4.a. (0.60 g) in methanol (5 mL), and the resulting solution was allowed to stir for 5 minutes. Sodium cyanoborohydride (0.18 g) in methanol (2 mL) was added, and the mixture was allowed to stir overnight at room temperature. The mixture was diluted with 1N sodium hydroxide (100 mL) and extracted with dichloromethane. The organic extracts were washed (brine) and evaporated to give the amine, which was used directly.

EXAMPLE 6

N-[2-(3,4-Dichlorophenyl)-4-[4-(N-phenylacetamido)-piperidino]butyl]-N-methylbenzamide To a flask containing methanol (0.5 mL) at 0° C. was added acetyl chloride (0.085 mL), and the resulting solution was allowed to stir for 20 minutes. 4-(N-Phenylacetamido)piperidine (0.327 g) in methanol (1 mL) was added, followed by N-[2-(3,4-dichlorophenyl)-4-oxobutyl]-N-methylbenzamide (0.350 g) in methanol (2.5 mL) and, 15 minutes later, sodium cyanoborohydride (0.038 g). After being stirred at room temperature for 4 hours, the reaction mixture was diluted with water and extracted with dichloromethane. The organic extracts were washed (water), dried, and evaporated. The resulting material was chromatographed, with ethyl acetate:methanol (5:1) as the eluent, to give the title compound (0.253 g) as a white solid; MS: m/z=552(M+1). Analysis for $C_{31}H_{35}Cl_2N_3O_2 \cdot 0.8\ H_2O$: Calculated: C, 65.67; H, 6.51; N, 7.41; Found: C, 65.76; H, 6.37; N, 7.48.

The intermediate 4-(N-phenylacetamido)piperidine was prepared as follows:

a. 8-Benzyloxycarbonyl-1,4-dioxa-8-azaspiro[4.5]decane. To a solution of 1,4-dioxa-8-azaspiro[4.5]decane (45.9 g) in dichloromethane (600 mL) was added N-(benzyloxycarbonyloxy)succinimide (81.5 g) in portions. After being stirred for 2 hours, the mixture was quenched with saturated aqueous sodium bicarbonate and stirred overnight as a biphasic mixture. The mixture was diluted with water (1 L), and the dichloromethane layer was dried and evaporated to give 8-benzyloxycarbonyl-1,4-dioxa-8-azaspiro[4.5]decane (86.0 g) as a colorless oil; MS: m/z=278(M+1); NMR: 7.35 (m,5), 5.13 (s,2), 3.96 (s,4), 3.59 (m,4), 1.67 (m,4).

b. 1-Benzyloxycarbonyl-4-piperidone. To a solution of 8-benzyloxycarbonyl-1,4-dioxa-8-azaspiro[4.5]decane (85 g) in tetrahydrofuran (500 mL) was added concentrated hydrochloric acid (100 mL) in water (200 mL), and the resulting solution was allowed to stir for 4 days. The mixture was diluted with water and extracted with dichloromethane. The organic extracts were washed (saturated aqueous sodium bicarbonate), dried, and evaporated to give the ketone (68.0 g) as an oil; MS: m/z=234(M+1); NMR: 7.37 (m,5), 5.18 (s,2), 3.80 (m,4), 2.46 (m,4).

c. 4-Anilino-1-benzyloxycarbonylpiperidine. To a flask containing methanol (40 mL) at 0° C. was added acetyl chloride (12.2 mL), and the resulting solution was allowed to stir for 20 minutes. To this mixture was added sequentially aniline (48 g) in methanol (214 mL), 1-benzyloxycarbonyl-4-piperidone (20 g), and sodium cyanoborohydride (3.28 g). After being stirred at room temperature for 5 hours, the reaction mixture was diluted with saturated aqueous sodium bicarbonate and extracted with dichloromethane. The combined organic extracts were washed (saturated aqueous sodium bicarbonate, water, 1N hydrochloric acid, saturated aqueous sodium bicarbonate, and water), dried, and evaporated to give the anilinopiperidine (19.0 g) as a brown oil; MS: m/z=311(M+1); NMR: 7.37 (m,5), 7.19 (m,2), 6.72 (m,1), 6.61 (m,2), 5.15 (s,2), 4.12 (m,2), 3.59 (m,1), 3.47 (m,1), 3.03 (m,2), 2.07 (m,2), 1.36 (m,2).

d. 1-Benzyloxycarbonyl-4-(N-phenylacetamido)piperidine. To a solution of 1-benzyloxycarbonyl-4-anilinopiperidine (5.0 g) in chloroform (75 mL) was added acetic anhydride (2.7 mL) and triethylamine (3.1 mL), and the resulting solution was allowed to stir overnight at room temperature, followed by 8 hours at reflux. The mixture was washed (1N hydrochloric acid, saturated aqueous sodium bicarbonate, water), dried, and evaporated to give the acetanilide (6.5 g) as an impure yellow oil; MS: m/z=353(M+1).

e. 4-(N-Phenylacetamido)piperidine. A solution of 1-benzyloxycarbonyl-4-(N-phenylacetamido)piperidine (6.5 g) and 20% palladium hydroxide on carbon (1.0 g) in ethanol (100 mL) was stirred overnight under hydrogen (1.01 bar). The mixture was filtered through diatomaceous earth, and the filtrate was evaporated. The resulting oil was dissolved in dichloromethane and extracted with 1N hydrochloric acid. The separated acidic aqueous phase was basified with 2N sodium hydroxide and extracted with dichloromethane. The combined organic extracts were dried and evaporated to give the acetanilide as a white solid (1.5 g); MS: m/z=219(M+1); NMR: 7.40 (m,3), 7.08 (m,2), 4.72 (m,1), 3.58 (m,1), 3.06 (m,2), 2.71 (m,2), 1.75 (m,5), 1.29 (m,2).

EXAMPLE 7

N-[2-(3,4-Dichlorophenyl)-4-[4-(2-oxopyrrolidin-1-yl)-piperidino]butyl]-N-methylbenzamide hydrochloride.

N-[2-(3,4-Dichlorophenyl)-4-oxobutyl]-N-methylbenzamide (870 mg) in methanol (2.4 mL) was added to a solution of 4-(2-oxopyrrolidin-1-yl)piperidine (0.460 g) and acetic acid (0.16 mL) in methanol (2.4 mL). After 5 minutes, sodium cyanoborohydride (0.173 g) in methanol (2.4 mL) was added in a single portion. After being stirred for 3 hours, the reaction mixture was diluted with aqueous sodium bicarbonate, stirred for 30 minutes, and extracted with dichloromethane. The organic extracts were dried, evaporated, and chromatographed, with dichloromethane:methanol (gradient 98:2, 90:10) as the eluent. The resulting material was dissolved in dichloromethane, precipitated out as the hydrochloride salt with ethereal hydrogen chloride, evaporated, and placed under high vacuum overnight to give the title compound (1.0 g) as a white solid; MS: m/z=502(M+1). Analysis for $C_{27}H_{33}Cl_2N_3O_2 \cdot 1.50\ HCl$: Calculated: C, 58.20; H, 6.24; N, 7.54; Found: C, 58.18; H, 6.27; N, 7.44.

The intermediate 4-(2-oxopyrrolidin-1-yl)piperidine was prepared as follows:

a. 1-Benzyloxycarbonyl-4-tert-butoxycarbonylaminopiperidine. To a solution of N-(benzyloxycarbonyloxy)succinimide (58.5 g) in dichloromethane (300 mL) was added sequentially triethylamine (36.0 mL) and 4-tert-butoxycarbonylaminopiperidine (from Example 1.j.) (47.0 g). After being stirred for 2 hours, the reaction mixture was washed (0.1N hydrochloric acid, dilute aqueous sodium bicarbonate), and the organic phase was dried and evaporated to give an oil. The addition of ether produced a precipitate that was filtered to give the 1-benzyloxycarbonyl-4-tert-butoxycarbonylaminopiperidine (75 g) as a white solid; NMR: 7.35 (m,5), 5.12 (s,2), 4.53 (1,m), 4.10 (m,2), 3.60 (m,1), 2.92 (m,2), 1.92 (m,2), 1.44 (s,9), 1.31 (m,2).

b. 4-Amino-1-benzyloxycarbonylpiperidine. To a solution of the above piperidine (55.0 g) in dichloromethane (300 mL) was added trifluoroacetic acid (90 mL) in 10 mL increments over a period of 20 minutes. After being stirred for 4 hours, the reaction mixture was diluted with water (1 L) and extracted with dichloromethane. The aqueous phase was basified with 1.0N sodium hydroxide (until pH 10) and extracted with dichloromethane. The combined organic extracts were dried and evaporated to give the amine as an oil that slowly solidified to a white solid (36.5 g); NMR: 7.36 (m,5), 5.12 (s,2), 4.12 (m,2), 2.83 (m,3), 1.80 (m,2), 1.51 (m,2), 1.25 (m,2).

c. 1-Benzyloxycarbonyl-4-(4-chlorobutyramido)piperidine. 4-Chlorobutyryl chloride (1.5 mL) was added to a solution of the above amine (2.5 g) and pyridine (1.8 mL) in dichloromethane (35 mL) cooled to 0° C. After being stirred for 3 hours at ambient temperature, the reaction mixture was diluted with 0.1N sodium hydroxide and stirred overnight. The separated dichloromethane layer was washed (1.0N hydrochloric acid, aqueous sodium bicarbonate), dried, and evaporated to give the amide as a white solid (3.0 g) by precipitation and filtration from ether; MS: m/z=303(M+1-HCl); NMR: 7.35 (m,5), 5.59 (d,1, J=7.7), 5.12 (s,2), 4.13 (m,2), 3.95 (m,1), 3.60 (m,2), 2.93 (m,2), 2.34 (m,2), 2.10 (m,2), 1.92 (m,2), 1.32 (m,2).

d. 1-Benzyloxycarbonyl-4-(2-oxopyrrolidin-1-yl)piperidine. The above amide (2.9 g) in tetrahydrofuran (20 mL) was cannulated into a solution of sodium hydride (0.412 g) in tetrahydrofuran (20 mL). After being stirred overnight, the reaction mixture was quenched with water, concentrated, diluted with water, and extracted with dichloromethane. The combined organic extracts were dried and evaporated. The resulting material was chromatographed, with ethyl acetate-:methanol (gradient 100:0, 90:10) as the eluent, to give the pyrrolidine as an oil (2.5 g); MS: m/z=303(M+1); NMR: 7.36 (m,5), 5.13 (s,2), 4.30 (m,2), 4.15 (m,1), 3.31 (m,2), 2.86 (m,2), 2.40 (m,2), 2.01 (m,2), 1.65 (m,4).

e. 4-(2-oxopyrrolidin-1-yl)piperidine. A solution of the above pyrrolidine (0.970 g) and 20% palladium hydroxide on carbon (0.100 g) in ethanol (15 mL) was stirred for 5 hours under hydrogen (1 bar). The reaction mixture was filtered through diatomaceous earth, and the filtrate was evaporated to give 4-(2-oxopyrrolidin-1-yl)-piperidine (0.50 g) as a hygroscopic semi-solid; MS: m/z=169(M+1); NMR (CD$_3$OD): 4.08 (m,1), 3.37 (m,2), 3.16 (m,2), 3.02 (m,1), 2.73 (m,2), 2.40 (m,2), 2.01 (m,2), 1.66 (m,4).

EXAMPLE 8

N-[2-(3,4-Dichlorophenyl)-4-[4-(2-oxopiperidino)-piperidino]butyl]-N-methylbenzamide hydrochloride.

Using a procedure similar to that described in Example 7, except replacing 4-(2-oxopyrrolidin-1-yl)piperidine with 4-(2-oxopiperidino)piperidine, the title compound was obtained as a white solid; MS: m/z=516(M+1). Analysis for C$_{28}$H$_{35}$Cl$_2$N$_3$O$_2$·2.20 HCl: Calculated: C, 56.36; H, 6.28; N, 7.04; Found: C, 56.37; H, 6.43; N, 6.94.

The intermediate 4-(2-oxopiperidino)piperidine was prepared as follows:

a. 1-Benzyloxycarbonyl-4-(5-chlorovaleramido)piperidine. 5-Chlorovaleryl chloride (1.8 mL) was added to a solution of 4-amino-1-benzyloxycarbonylpiperidine (3.0 g) and pyridine (2.2 mL) in dichloromethane (40 mL) at 0° C. After being stirred overnight at ambient temperature, the reaction mixture was diluted with dichloromethane, washed (water, aqueous copper(II) sulfate, and water), dried, evaporated, suspended in ether, and filtered to give the amide (3.7 g) as a white solid; MS: m/z=353(M+1), 317(M+1-HCl); NMR: 7.35 (m,5), 5.43 (d,1, J=7.7), 5.12 (s,2), 4.13 (m,2), 3.93 (m,1), 3.54 (m,2), 2.92 (m,2), 2.18 (m,2), 1.92 (m,2), 1.78 (m,4), 1.29 (m,2).

b. 1-Benzyloxycarbonyl-4-(2-oxopiperidino)piperidine. Using a procedure similar to that described in Example 7.d., except replacing 1-benzyloxycarbonyl-4-(4-chlorobutyramido)piperidine with 1-benzyloxycarbonyl-4-(5-chlorovaleramido)piperidine, 1-benzyloxycarbonyl- 4-(2-oxopiperidino)piperidine was obtained as an oil; MS: m/z=317(M+1); NMR: 7.36 (m,5), 5.13 (s,2), 4.71 (m,1), 4.26 (m,2), 3.13 (m,2), 2.89 (m,2), 2.41 (m,2), 1.76 (m,2), 1.61 (m,4).

c. 4-(2-Oxopiperidino)piperidine. Using a procedure similar to that described in Example 7.e., except replacing 1-benzyloxycarbonyl- 4-(2-oxopyrrolidin-1-yl)piperidine with 1-benzyloxycarbonyl-4-(2-oxopiperidino)piperidine, 4-(2-oxopiperidino)piperidine was obtained as a white solid; MS: m/z=183(M+1); NMR (CD$_3$OD): 4.48 (m,1), 3.27 (m,2), 3.12 (m,2), 2.68 (m,2), 2.36 (m,2), 1.83–1.58 (m,8).

EXAMPLE 9

(S)-N-[2-(3,4-Dichlorophenyl)-4-[4-(2-thioxopiperidino)-piperidino]butyl]-N-methylbenzamide hydrochloride.

Using a procedure similar to that described in Example 7, except replacing 4-(2-oxopyrrolidin-1-yl)piperdine with 4-(2-thioxopiperidino)piperidine and N-[2-(3,4-dichlorophenyl)-4-oxobutyl]-N-methylbenzamide with (S)-N-[2-(3,4-dichlorophenyl)-4-oxobutyl]-N-methylbenzamide, the title hydrochloride was obtained as a white solid; MS: m/z=532(M+1); Analysis for C$_{28}$H$_{35}$Cl$_2$N$_3$OS·1.40 HCl: Calculated: C, 57.62; H, 6.29; N, 7.20; Found: C, 57.64; H, 6.55; N, 6.93.

The (S)-N-[2-(3,4-dichlorophenyl)-4-oxobutyl]-N-methylbenzamide was prepared as follows:

a. 2-(3,4-Dichlorophenyl)-4-hydroxybutylamine. To a mechanically stirred solution of 2-(3,4-dichlorophenyl)-4-(tetrahydropyran-2-yloxy)butylamine (550 g) in methanol (3.3 L) was added in one portion 6.0N hydrochloric acid (352 mL), resulting in a slight exotherm. After being stirred for 3 hours, the reaction mixture was evaporated, and the residue was diluted with water to 3 L volume. This solution was extracted with ether (2 times 500 mL), basified with sodium hydroxide pellets (100 g), and extracted with ethyl acetate (4 times 500 mL). The combined ethyl acetate extracts were washed (800 mL saturated sodium chloride), dried, and evaporated to give the alcohol as an amber oil (367 g) that solidified under high vacuum; NMR: 7.39 (d,1, J=8.2), 7.28 (d,1, J=2.0), 7.04 (dd,1, J=8.2, 2.0), 3.65 (m,1), 3.50 (m,1), 2.90 (m,2), 2.71 (m,1), 2.25 (m,2), 1.86 (m,2).

b. (S)-2-(3,4-Dichlorophenyl)-4-hydroxybutylamine. To a mechanically stirred solution of D-tartaric acid (222 g) in methanol (4 L) at reflux was added the above alcohol (342 g) in warm methanol (2 L) in one portion followed by additional methanol (1L). The mixture was heated to reflux. Crystals began to form before attaining the boiling point. After 1.5 hours at reflux, the solution was gradually cooled to room temperature and stirred for 3 days. The first crop of tartrate salt was collected by suction filtration and dried in a vacuum oven at 60° C. to give the product (232 g). This material was taken up in methanol (13.5 L) at boiling, and held at reflux for 1 hour allowing 1 L of methanol to distill off. The mixture was allowed to cool gradually to room temperature and stirred for 4 days. The first crop of crystals was collected by suction filtration and dried to give a solid (178.8 g). The methanol filtrate was evaporated to approximately 3 L volume. The resulting suspension was heated back to reflux to give a clear solution that was allowed to cool gradually to room temperature with stirring. A second crop of crystals (43.8 g) was collected. The combined crops of resolved amino alcohol tartrates (222.6 g) were taken up in 1.0N sodium hydroxide (1.5 L) and extracted with dichloromethane (4 times 500 mL). The combined organic extracts were washed (brine), dried, and evaporated to give the optically enriched alcohol (135.4 g) as an off-white solid; mp 80°–2° C.; MS: m/z=324(M+1); NMR (CD$_3$OD): 7.47

(d,1, J=8.3), 7.42 (d,1, J=2.1), 7.17 (dd,1, J=8.2, 2.1), 3.47 (m,1), 3.34 (m,1), 2.83 (m,3), 1.92 (m,1), 1.74 (m,1).

c. Ethyl (S)-N-[2-(3,4-dichlorophenyl)-4-hydroxybutyl]-carbamate. Ethyl chloroformate (25.5 g) was added dropwise over 20 minutes to a mechanically stirred solution of the above alcohol (50.0 g) and triethylamine (24.9 g) in dichloromethane (600 mL). The internal temperature was maintained at −20° to −25° C. during the addition. The reaction mixture was allowed to warm gradually to room temperature over a 4 hour period, and was washed (1N hydrochloric acid, saturated aqueous sodium bicarbonate, and saturated aqueous sodium chloride). The separated dichloromethane phase was dried and evaporated to give the carbamate as a yellow oil (65.3 g); MS: m/z=306(M+1); NMR (CD$_3$OD): 7.44 (d,1, J=8.3), 7.38 (d,1, J=2.1), 7.15 (dd,1, J=8.3, 2.1), 3.99 (q,2, J=7.1), 3.45 (m,1), 3.29 (m,3), 2.97 (m,1), 1.92 (m,1), 1.75 (m,1), 1.16 (t,3, J=7.1).

d. (S)-N-[2-(3,4-Dichlorophenyl)-4-hydroxybutyl]methylamine. The above carbamate (65.3 g) in tetrahydrofuran (500 mL) was added dropwise over 30 minutes to a mechanically stirred supension of lithium aluminum hydride (16.0 g) in tetrahydrofuran (200 mL). The internal temperature rose to 45° C. during the addition. The reaction mixture was heated at reflux for 1 hour, cooled to room temperature and stirred overnight. The mixture was cooled in an ice bath, and saturated aqueous sodium sulfate (50 mL) was added dropwise over 45 minutes. After an additional hour of stirring, solid anhydrous sodium sulfate (50 g) was added. After being stirred for 30 minutes, the mixture was filtered through diatomaceous earth, and the filtrate was evaporated to give the amine (52.9 g) as a yellow oil; MS: m/z=248(M+1); NMR: 7.37 (d,1, J=8.2), 7.27 (d,1, J=2.0), 7.01 (dd,1, J=8.2, 2.1), 3.69 (m,1), 3.53 (m,1), 3.40 (m,2), 2.76 (m,3), 2.45 (m,3), 1.89 (m,2).

e. (S)-N-[2-(3,4-Dichlorophenyl)-4-hydroxybutyl]-N-methylbenzamide. Benzoyl chloride (31.5 g) in dichloromethane (200 mL) was added dropwise over 45 minutes to a mechanically stirred solution of the above amine (52.9 g) and triethylamine (54.0 g) in dichloromethane (1 L). An ice bath was used throughout the addition to maintain an internal temperature of 5°–8° C. The reaction mixture was stirred for 3 hours at room temperature, and washed (1N hydrochloric acid, brine). The separated dichloromethane layer was evaporated to give a yellow oil which was chromatographed, with dichloromethane:-methanol (gradient 100:0, 95:5) as the eluent, to give the benzamide (65.6 g) as a white solid; mp 123°–5° C.; MS: m/z=352(M+1); [α]$_D$=−18.3° (c=2.46, CH$_3$OH).

f. (S)-N-[2-(3,4-Dichlorophenyl)-4-oxobutyl]-N-methyl benzamide. The above benzamide (12.9 g) in dichloromethane (150 mL) was cannulated into a solution of 1,1,1-triacetoxy-1,1-dihydro-1,2-benziodoxol- 3-(1H)-one (18.6 g) and tert-butanol (4.5 mL) in dichloromethane (150 mL). After being stirred for 5 minutes, the reaction mixture was diluted with ether (600 mL) and a solution of sodium bicarbonate (19.7 g) and sodium thiosulfate pentahydrate (64.5 g) in water (825 mL). The biphasic system was vigorously stirred until both layers became clear (approximately 30 minutes). The separated organic layer was washed (saturated aqueous sodium bicarbonate), dried, and evaporated. The crude material was chromatographed, with dichloromethane:ether (1:1) as the eluent, to give the aldehyde as a white solid (9.7 g) following precipitation and filtration from ether; MS: m/z=350(M+1).

The intermediate 4-(2-thioxopiperidino)piperidine was prepared as follows:

g. 1-Benzyloxycarbonyl-4-(2-thioxopiperidino)piperidine. 1-Benzyloxycarbonyl-4-(2-oxopiperidino)piperidine (3.1 g) in tetrahydrofuran (10 mL) was cannulated into a suspension of 2,4-bis( 4-methoxyphenyl)-2,4-dithioxo-1,3, 2,4-dithiadiphosphetane (2.0 g) in tetrahydrofuran (40 mL). Within 5 minutes a clear solution was obtained. After being stirred for 20 minutes, the reaction mixture was evaporated and chromatographed, with dichloromethane:ether (gradient 90:10, 83:17) as the eluent, to give the thio compound (2.9 g) as a viscous oil; MS: m/z=333(M+1); NMR: 7.35 (m,5), 5.79 (m,1), 5.14 (s,2), 4.32 (m,2), 3.27 (m,2), 3.04 (m,2), 2.92 (m,2), 1.82 (m,4), 1.72 (m,2), 1.61 (m,2).

h. 4-(2-Thioxopiperidino)piperidine. Trifluoromethanesulfonic acid (3.4 mL) was added dropwise to a solution of the above piperidine (2.4 g) and anisole (2.5 mL) in dichloromethane (40 mL) at 0° C. The reaction mixture was stirred for 30 minutes, and solid potassium carbonate/sodium sulfate was added to give a solid mass. The solid was collected by filtration, suspended in a mixture of dichloromethane and methanol, and filtered. The filtrate was evaporated to give an amorphous solid that was passed through a column of a weak base ion exchange resin followed by a column of reversed phase silica gel with methanol as the the eluent in each. The resulting material was dissolved in dichloromethane and filtered to remove undissolved white solid. The filtrate was evaporated and chromatographed, with dichloromethane:methanol (gradient 95:5, 90:10) as the eluent, to give the piperidine (0.930 g) as a white, amorphous solid; MS: m/z=199(M+1); NMR (CD$_3$OD): 5.79 (m,1), 3.50 (m,2), 3.41 (m,2), 3.31 (m,1), 3.12 (m,2), 2.98 (m,2), 2.09–1.84 (m,6), 1.72 (m,2).

EXAMPLE 10

N-[2-(3,4-Dichlorophenyl)-4-[4-(N-methylacetamido)-piperidino]butyl]-N-methylbenzamide.

Using a procedure similar to that described in Example 7, except replacing 4-(2-oxopyrrolidin-1-yl)piperidine with 4-(N-methylacetamido)piperidine and omitting the treatment with ethereal hydrogen chloride, the title compound was obtained as a white solid; MS: m/z=490(M+1). Analysis for C$_{26}$H$_{33}$Cl$_2$N$_3$O$_2$·0.50 H$_2$O: Calculated: C, 62.52; H, 6.86; N, 8.41; Found: C, 62.56; H, 6.50; N, 8.70.

The intermediate 4-(N-methylacetamido)piperidine was prepared as follows:

a. 4-Acetamido-1-benzyloxycarbonylpiperidine. Acetic anhydride (4.4 mL) was added to a solution of 4-amino-1-benzyloxycarbonylpiperidine (10 g) and triethylamine (6.5 mL) in dichloromethane (200 mL). After being stirred overnight, the reaction mixture was washed (1.0N hydrochloric acid, aqueous sodium bicarbonate, water), dried, and evaporated. A solution of the crude product in tetrahydrofuran and 1.0N sodium hydroxide (to remove excess anhydride) was stirred for 2 hours, evaporated to an aqueous mixture, and extracted with dichloromethane. The organic extracts were dried and evaporated to give an off-white solid. This material was suspended in ether and filtered to give the acetamide (10.3 g) as a white solid; MS: m/z= 277(M+1), 233[(M+1)-acetyl]; NMR: 7.34 (m,5), 5.51 (d,1, J=7.2), 5.11 (s,2), 4.12 (m,2), 3.92 (m,1), 2.91 (m,2), 1.96 (s,3), 1.91 (m,2), 1.29 (m,2).

b. 1-Benzyloxycarbonyl-4-(N-methylacetamido)piperidine. To a suspension of sodium hydride (500 mg, 97%) in dimethylformamide (25 mL) was added the above acetamide (2.3 g). After 15 minutes, iodomethane (1.0 mL) was dropped in. After being stirred for 3 hours, the reaction mixture was quenched slowly with water, diluted with water (1.5 L), and extracted with dichloromethane. The organic extracts were dried and evaporated to give the title compound (2.3 g) as a viscous oil; MS: m/z=291(M+1), 247 [(M+1)-acetyl].

c. 4-(N-Methylacetamido)piperidine. Using a procedure similar to that described in Example 7.e., except replacing 1-benzyloxycarbonyl- 4-(2-oxopyrrolidin-1-yl)piperidine with 1-benzyloxycarbonyl- 4-(N-methylacetamido)piperidine, 4-(N-methylacetamido)piperidine was obtained as an oil; MS: m/z=157(M+1); NMR (CD$_3$OD): ca. 1.3:1 mixture of rotamers, 4.46 (m,0.56), 3.79 (m,0.44), 3.10 (m,2), 2.91 (s,1.68), 2.80 (s,1.32), 2.67 (m,2), 2.14 (s,1.32), 2.09 (s,1.68), 1.74–1.54 (m,4).

EXAMPLE 11

N-[4-[4-(N-Allylacetamido)piperidino]-2-(3,4-dichlorophenyl)butyl]-N-methylbenzamide hydrochloride Using a procedure similar to that described in Example 7, except replacing 4-(2-oxopyrrolidin-1-yl)piperidine with 4-(N-allylacetamido)piperidine, the title compound was obtained as a white solid; MS: m/z=516(M+1). Analysis for $C_{28}H_{35}Cl_2N_3O_2 \cdot 2.0$ HCl: Calculated: C, 57.06; H, 6.33; N, 7.13; Found: C, 56.91; H, 6.31; N, 7.13.

The intermediate 4-(N-allylacetamido)piperidine was prepared as follows:

a. 4-(N-Allylacetamido)-1-benzyloxycarbonylpiperidine. Using a procedure similar to that described in Example 7.b., except replacing iodomethane with allyl bromide, 4-(N-allylacetamido)-1-benzyloxycarbonylpiperidine was obtained as an oil; MS: m/z=317(M+1), 273[(M+1)-acetyl]; NMR (CDCl$_3$/CF$_3$COOH): 7.36 (m,5), 5.76 (m,1), 5.36 (m,1), 5.23 (m,1), 5.16 (s,2), 4.65 (m,1), 4.30 (m,2), 3.99 (m,2), 2.92 (m,2), 2.30 (s,3), 1.78 (m,2), 1.66 (m,2).

b. 4-(N-Allylacetamido)piperidine. Iodotrimethylsilane (2.7 mL) was added dropwise to a solution of 4-(N-allylacetamido)-1-benzyloxycarbonylpiperidine (1.5 g) in acetonitrile (30 mL) at 0° C. After being stirred for 20 minutes, the reaction mixture was evaporated, dissolved in 1.0N hydrochloric acid, and extracted with dichloromethane (discarded). The acidic aqueous layer was basified with 1.0N sodium hydroxide and extracted with dichloromethane. The organic extracts were dried and evaporated to give the title compound (0.72 g) as an oil; MS: m/z=183(M+1); NMR (CD$_3$OD): ca. 2:1 mixture of rotamers, 5.88 (m,1), 5.27–5.07 (m,2), 4.44 (m,0.7), 3.98 (m,2.3), 3.24 (m,1.7), 2.99 (m,0.3), 2.83 (m,1.7), 2.58 (m,0.3), 2.19 (m,0.9), 2.09 (m,2.1), 1.87–1.67 (m,4).

EXAMPLE 12

N-[2-(3,4-Dichlorophenyl)-4-[4-(N-propylacetamido)-piperidino]butyl]-N-methylbenzamide hydrochloride Using a procedure similar to that described in Example 7, except replacing 4-(2-oxopyrrolidin-1-yl)piperidine with 4-(N-propylacetamido)piperidine, the title compound was obtained as a white solid; MS: m/z=518(M+1). Analysis for $C_{28}H_{37}Cl_2N_3O_2 \cdot 1.9$ HCl: Calculated: C, 57.21; H, 6.67; N, 7.15; Found: C, 57.25; H, 6.97; N, 6.94.

The intermediate 4-(N-propylacetamido)piperidine was prepared as follows:

a. 4-(N-Propylacetamido)piperidine. Using a procedure similar to that described in Example 7.e., except replacing 1-benzyloxycarbonyl- 4-(2-oxopyrrolidin-1-yl)piperidine with 1-benzyloxycarbonyl-4-(N-allylacetamido)piperidine, 4-(N-propylacetamido)piperidine was obtained as an oil; MS: m/z=185(M+1); NMR: ca. 2:1 mixture of rotamers, 4.45 (m, 0.65), 3.57 (0.35), 3.15 (m,4), 2.69 (m,2), 2.26 (m,1), 2.13 (s,1.05), 2.11 (s,1.95), 1.74–1.51 (m,6), 0.90 (m,3).

EXAMPLE 13

N-[2-(3,4-Dichlorophenyl)-4-[4-(N-isopropylacetamido)-piperidino]butyl]-N-methylbenzamide hydrochloride Using a procedure similar to that described in Example 7, except replacing 4-(2-oxopyrrolidin-1-yl)piperidine with 4-(N-isopropylacetamido)piperidine, the title compound was obtained as a white solid; MS: m/z=518(M+1). Analysis for $C_{28}H_{37}Cl_2N_3O_2 \cdot 2.8$ HCl: Calculated: C, 54.19; H, 6.46; N, 6.77; Found: C, 54.29; H, 6.74; N, 6.39.

The intermediate 4-(N-isopropylacetamido)piperidine was prepared as follows:

a. 1-Benzyloxycarbonyl-4-(isopropylamino)piperidine. 1-Benzyloxycarbonyl-4-oxopiperidine (2.0 g) in methanol (5 mL) was added to a solution of isopropylamine (1.5 mL) and acetic acid (1.0 mL) in methanol (30 mL). After 10 minutes, sodium cyanoborohydride (1.1 g) in methanol (3 mL) was added in a single portion. After being stirred overnight, the reaction mixture was diluted with aqueous sodium bicarbonate, stirred for 30 minutes, and extracted with dichloromethane. The organic extracts were concentrated and dissolved in 1.0N hydrochloric acid. The acidic aqueous solution was extracted with dichloromethane (discarded), basified with 1.0N sodium hydroxide, and extracted with dichloromethane. The organic extracts were dried and evaporated to give the title compound (1.0 g) as an oil; MS: m/z=277(M+1); NMR (CDCl$_3$/CF$_3$COOH): 7.34 (m,5), 5.16 (s,2), 4.35 (m,2), 3.60 (m,1), 3.46 (m,1), 2.92 (m,2), 2.08 (m,2), 1.65 (m,2), 1.38 (d,6, J=6.5).

b. 1-Benzyloxycarbonyl-4-(N-isopropylacetamido)piperidine. Using a procedure similar to that described in Example 10.a., except replacing 4-amino-1-benzyloxycarbonylpiperidine with 1-benzyloxycarbonyl-4-(N-isopropylamino)piperidine, the title compound was obtained as an oil after chromatography, with dichloromethane:methanol (gradient 98:2, 96:4) as the eluent; MS: m/z=319(M+2); NMR (CDCl$_3$/CF$_3$COOH): ca. 1.6:1 mixture of rotamers, 7.35 (m,5), 5.17 (m,2), 4.34 (m,2), 4.17 (m,0.6), 3.91 (m,0.4), 3.83–3.50 (m,1), 2.90 (m,2), 2.45 (m,4), 1.87 (m,2), 1.62 (m,1), 1.41 (d,2.4, J=6.8), 1.36 (d,3.6, J=6.7).

c. 4-(N-Isopropylacetamido)piperidine. Using a procedure similar to that described in Example 7.e., except replacing 1-benzyloxycarbonyl-4-(2-oxopyrrolidin-1-yl)piperidine with 1-benzyloxycarbonyl-4-(N-isopropylacetamido)piperidine, 4-(N-isopropylacetamido)piperidine was obtained as an oil; MS: m/z=277(H+1); NMR: ca. 1:1 mixture of rotamers, 3.93 (m,0.5), 3.50 (m,0.5), 3.15 (m,2), 2.63 (m,2), 2.48 (m,1), 2.10 (m,4), 1.70 (m,2), 1.48 (m,1), 1.37 (d,3, J=6.8), 1.22 (d,3, J=6.8).

EXAMPLE 14

N-[2-(3,4-Dichlorophenyl)-4-[4-(N-ethylpropionamido)-piperidino]butyl]-N-methylbenzamide hydrochloride Using a procedure similar to that described in Example 7, except replacing 4-(2-oxopyrrolidin-1-yl)piperidine with 4-(N-ethylpropionamido)piperidine, the title compound was obtained as a white solid; MS: m/z=518(M+1). Analysis for $C_{28}H_{37}Cl_2N_3O_2 \cdot 1.6$ HCl: Calculated: C, 58.30; H, 6.74; N, 7.28; Found: C, 58.23; H, 6.73; N, 7.17.

The intermediate 4-(N-ethylpropionamido)piperidine was prepared as follows:

a. 1-Benzyloxycarbonyl-4-(N-ethyl-N-tert-butoxycarbonylamino)-piperidine. To a suspension of sodium hydride (4.0 g) in dimethylformamide (100 mL) was added 1-benzyloxycarbonyl-4-tertbutoxycarbonylaminopiperidine (46.7 g) in dimethylformamide (50 mL). After 20 minutes, iodoethane (22.0 mL) was dropped in slowly over a period of 2 hours. After being stirred overnight, the reaction mixture was slowly quenched with water, diluted with water (1.5 L), and extracted with dichloromethane (3 times 100 mL). The organic extracts were dried and evaporated to give the title compound (50.6 g) as an oil; MS: m/z=263[(M+1)-tert-butoxycarbonyl].

b. 1-Benzyloxycarbonyl-4-(ethylamino)piperidine. Trifluoroacetic acid (108 mL) was added to a solution of the above piperidine (50.6 g) in dichloromethane (200 mL) resulting in vigorous evolution of gas. After being stirred for 3 hours, the reaction mixture was evaporated, dissolved in dilute aqueous hydrochloric acid, and extracted with ethyl acetate (discarded). The acidic aqueous layer was basified with 1.0N sodium hydroxide until a pH of 10 was attained, and extracted with dichloromethane. The organic extracts were dried, evaporated, and distilled (178°–179° C., 8.7 Pa) to give the title compound (30.0 g) as a colorless oil; MS: m/z=263(M+1); NMR ($CD_3OD/CF_3COOH$): 7.35 (m,5), 5.13 (s,2), 4.27 (m,2), 3.32 (m,1), 3.10 (q,2, J=7.3), 2.91 (m,2), 2.09 (m,2), 1.49 (m,2), 1.31 (t,3, J=7.3).

c. 1-Benzyloxycarbonyl-4-(ethylpropionamido)piperidine. Using a procedure similar to that described in Example 10.a., except replacing 4-amino-1-benzyloxycarbonylpiperidine with 1-benzyloxycarbonyl- 4-(N-ethylamino)piperidine and acetic anhydride with propionic anhydride, the title compound was obtained as an oil; MS: m/z=319(M+1); NMR: ca. 1.5:1 mixture of rotamers, 7.36 (m,5), 5.13 (m,2), 4.59 (m,0.58), 4.28 (m,2), 3.74 (m,0.42), 3.22 (m,2), 2.84 (m,2), 2.34 (m,2), 1.64 (m,4), 1.13 (m,6).

d. 4-(N-Ethylpropionamido)piperidine. Using a procedure similar to that described in Example 7.e., except replacing 1-benzyloxycarbonyl-4-(2-oxopyrrolidin-1-yl)piperidine with 1-benzyloxycarbonyl-4-(N-ethylpropionamido)piperidine, 4-(N-ethylpropionamido)piperidine was obtained as an oil; MS: m/z=185(M+1); NMR ($CD_3OD$): ca. 1:1 mixture of rotamers, 4.34 (m,0.47), 3.79 (m,0.53), 3.32 (m,2), 3.09 (m,2), 2.63 (m,2), 2.40 (m,2), 1.68 (m,4), 1.22–1.08 (m,6).

EXAMPLES 15–20

Using a procedure similar to that described in Example 7, except substituting the requsite piperidine for the 4-(2-oxopyrrolidin- 1-yl)piperidine used therein, the following compounds of formula I were prepared.

EXAMPLE 15

N-[2-(3,4-Dichlorophenyl)-4-[4-(N-ethylbutyramido)-piperidino]butyl]-N-methylbenzamide hydrochloride; MS: m/z=532(M+1). Analysis for $C_{29}H_{39}Cl_2N_3O_2 \cdot 1.3$ HCl: Calculated: C, 60.06; H, 7.00; N, 7.24; Found: C, 60.11; H, 7.07; N, 6.97.

EXAMPLE 16

N-[2-(3,4-Dichlorophenyl)-4-[4-(N-ethylisobutyramido)-piperidino]butyl]-N-methylbenzamide hydrochloride; MS: m/z=532(M+1). Analysis for $C_{29}H_{39}Cl_2N_3O_2 \cdot 1.35$ HCl: Calculated: C, 59.87; H, 6.99; N, 7.22; Found: C, 59.90; H, 7.03; N, 7.37.

EXAMPLE 17

N-[2-(3,4-Dichlorophenyl)-4-[4-(N-ethyltrifluoroacetamido)piperidino]butyl]-N-methylbenzamide hydrochloride; MS: m/z=558(M+1). Analysis for $C_{27}H_{32}Cl_2F_3N_3O_2 \cdot 1.75$ HCl: Calculated: C, 52.11; H, 5.47; N, 6.75; Found: C, 52.08; H, 5.59; N, 7.13.

EXAMPLE 18

N-[2-(3,4-Dichlorophenyl)-4-[4-(N-ethyl-N'-methylureido)piperidino]butyl]-N-methylbenzamide hydrochloride; MS: m/z=519(M+1). Analysis for $C_{27}H_{36}Cl_2N_42 \cdot 0.7$ $H_2O$: Calculated: C, 60.94; H, 7.08; N, 10.53; Found: C, 60.93; H, 6.84; N, 10.85.

EXAMPLE 19

N-[2-(3,4-Dichlorophenyl)-4-[4-(N-ethyl-N',N'-dimethylureido)piperidino]butyl]-N-methylbenzamide hydrochloride; MS: m/z=533(M+1). Analysis for $C_{28}H_{38}Cl_2N_42 \cdot 1.45$ HCl: Calculated: C, 57.35; H, 6.78; N, 9.55; Found: C, 57.35; H, 6.73, N, 9.52.

EXAMPLE 20

N-[2-(3,4-Dichlorophenyl)-4-[4-(N-ethylformamido)piperidino]butyl]-N-methylbenzamide hydrochloride; MS: m/z=490(M+1). Analysis for $C_{26}H_{33}Cl_2N_3O_2 \cdot 2.0$ HCl: Calculated: C, 55.43; H, 6.26; N, 7.46; Found: C, 55.53; H, 6.17; N, 7.78.

The starting material piperidines for Examples 15–20 were prepared as follows.

EXAMPLES 15.a.–20.a.

EXAMPLE 15.a.

1-Benzyloxycarbonyl-4-(N-ethylbutyramido)piperidine. Using a procedure similar to that described in Example 10.a., except replacing 4-amino-1-benzyloxycarbonylpiperidine with 1-benzyloxycarbonyl-4-(N-ethylamino)piperidine and acetic anhydride with burytic anhydride, the amide was obtained as an oil; MS: m/z=333(M+1); NMR: ca. 1:1 mixture of rotamers, 7.36 (m,5), 5.13 (m,2), 4.58 (m,0.5), 4.28 (m,2), 3.74 (m,0.5), 3.22 (m,2), 2.84 (m,2), 2.29 (m,2), 1.67 (m,6), 1.14 (m,3), 0.96 (m,3).

EXAMPLE 16.a.

1-Benzyloxycarbonyl-4-(N-ethylisobutyramido)-piperidine. Using a procedure similar to that described in Example 10.a., except replacing 4-amino-1-benzyloxycarbonylpiperidine with 1-benzyloxycarbonyl-4-(N-ethylamino)piperidine and acetic anhydride with isobutyric anhydride, the amide was obtained as an oil; MS: m/z=333(M+1), 289[(M+1)-acetyl]; NMR: ca. 1.3:1 mixture of rotamers, 7.35 (m,5), 5.12 (m,2), 4.59 (m,0.57), 4.28 (m,2), 3.74 (m,0.43), 3.21 (m,2), 2.84 (m,2), 2.72 (m,1), 1.63 (m,4), 1.10 (m,9).

EXAMPLE 17.a.

1-Benzyloxycarbonyl-4-(N-ethyltrifluoroacetamido)-piperidine. Trifluoroacetic anhydride (1.6 mL) was added to a solution of 1-benzyloxycarbonyl-4-(N-ethylamino)piperidine (2.0 g) and triethylamine (1.7 mL) in dichloromethane (40 mL). After being stirred for 3 hours, the reaction mixture was washed (1.0N hydrochloric acid, aqueous sodium bicarbonate, water), dried, and evaporated to give the amide (2.0 g) as an oil; MS: m/z=359(M+1); NMR (CDCl$_3$/CF$_3$COOH): ca. 1.3:1 mixture of rotamers, 7.36 (m,5), 5.18 (s,2), 4.35 (m,2), 4.20 (m,0.56), 3.98 (m,0.44), 3.50 (m,0.88), 3.42 (m,1.12), 2.93 (m,2), 1.83 (m,4), 1.29 (t,1.32, J=7.1), 1.21 (t,1.68, J=7.0).

EXAMPLE 18.a.

1-Benzyloxycarbonyl-4-(N-ethyl-N'-methylureido)-piperidine. A solution of 1-benzyloxycarbonyl-4-(N-ethylamino)-piperidine (4.0 g) and methyl isocyanate (11 mL) was stirred for 30 hours at ambient temperature. The reaction mixture was diluted with chloroform and evaporated to give the urea as an oil; MS: m/z=320(M+1). The material was used without further purification.

EXAMPLE 19.a.

1-Benzyloxycarbonyl-4-(N-ethyl-N',N'-dimethylureido)-piperidine. Using a procedure similar to that described in Example 10.b., except replacing 1-benzyloxycarbonyl-4-(N-methylacetamido)piperidine with 1-benzyloxycarbonyl-4-(N-ethyl-N'-methylureido)piperidine, the N',N'-dimethylureido compound was obtained as an oil after chromatography, with dichloromethane:methanol (gradient 98:2, 96:4) as the eluent; MS: m/z=334(M+1); NMR (CDCl$_3$/CF$_3$COOH): 7.36 (m,5), 5.16 (s,2), 4.31 (m,2), 3.82 (m,1), 3.35 (q,2, J=7.1), 3.06 (s,6), 2.89 (m,2), 1.82 (m,4), 1.16 (t,3, J=7.1).

EXAMPLE 20.a.

1-Benzyloxycarbonyl-4-(N-ethylformamido)piperidine. A stirred solution of 1-benzyloxycarbonyl-4-(N-ethylamino)piperidine (1.5 g) in triethyl orthoformate (10 mL) containing a catalytic amount of p-toluenesulfonic acid was heated at 90° C. for 12 hours. The reaction mixture was diluted with 1.0N hydrochloric acid (10 mL), stirred for 30 minutes, diluted with water, and extracted with dichloromethane. The organic extracts were washed (aqueous sodium bicarbonate, water), dried, and evaporated to an oil that slowly solidified. The solid was suspended in ether and filtered to give the formamido compound (1.0 g) as a white solid; MS: m/z=291(M+1); NMR: ca. 1.5:1 mixture of rotamers, 8.15 (s,0.6), 8.11 (s,0.4), 7.36 (m,5), 5.14 (m,2), 4.30 (m,2.4), 3.43 (m,0.6), 3.25 (m,2), 2.82 (m,2), 1.73 (m,4), 1.21 (t,1.2, J=7.2), 1.15 (t,1.8, J=7.1).

EXAMPLES 15.b.–20.b.

Using a procedure similar to that described in Example 7.e., except replacing 1-benzyloxycarbonyl-4-(2-oxopyrrolidin-1-yl)-piperidine with the requisite 1-benzyloxycarbonyl protected piperidine, prepared as described in Examples 15.a.–20.a. above, the following compounds were prepared.

EXAMPLE 15.b.

4-(N-ethylbutyramido)piperidine; MS: m/z=199(M+1); NMR (CD$_3$OD): ca. 1:1 mixture of rotamers, 4.34 (m,0.5), 3.82 (m,0.5), 3.33 (m,2), 3.12 (m,2), 2.68 (m,2), 2.37 (m,2), 1.78–1.58 (m,6), 1.21 (t,1.5, J=7.1), 1.11 (t,1.5, J=7.0), 0.96 (m,3).

EXAMPLE 16.b.

4-(N-ethylisobutyramido)piperidine; MS: m/z=198(M+1); NMR (CD$_3$OD): ca. 1:1 mixture of rotamers, 4.35 (m,0.5), 3.87 (m,0.5), 3.33 (m,2), 3.10 (m,2), 2.93 (m,0.5), 2.83 (m,0.5), 2.64 (m,2), 2.40 (m,0.5), 1.70 (m,3.5), 1.23–1.07 (m,9).

EXAMPLE 17.b.

4-(N-ethyltrifluoroacetamido)piperidine; MS: m/z=225(M+1); NMR: 3.82 (m,1), 3.42 (m,2), 3.25 (m,2), 2.71 (m,2), 1.99–1.74 (m,4), 1.21 (m,3).

EXAMPLE 18.b.

4-(N-ethyl-N'-methylureido)piperidine; MS: m/z=186(M+1); NMR (CD$_3$OD/CF$_3$COOH): 4.22 (m,1), 3.48 (m,2), 3.23 (q,2, J=7.1), 3.09 (m,2), 2.76 (s,3), 2.07 (m,2), 1.90 (m,2), 1.16 (t,3, J=7.1).

EXAMPLE 19.b.

4-(N-ethyl-N',N'-dimethylureido)piperidine; MS: m/z=200(M+1); NMR (CD$_3$OD/CF$_3$COOH): 3.59 (m,1), 3.44 (m,2), 3.16 (q,2, J=7.1), 3.05 (m,2), 2.85 (m,6), 2.09 (m,2), 1.95 (m,2), 1.08 (t,3, J=7.1).

EXAMPLE 20.b.

4-(N-ethylformamido)piperidine; MS: m/z=157(M+1); NMR: ca. 1.5:1 mixture of rotamers, 8.15 (s,0.6), 8.11 (s,0.4), 4.21 (m,0.4), 3.31 (m,2.6), 3.17 (m,2), 2.68 (m,2), 1.96 (m,1), 1.74 (m,4), 1.23 (t,1.2, J=7.2), 1.17 (t,1.8, J=7.1).

EXAMPLE 21

(S)-N-[2-(3,4-Dichlorophenyl)-4-[4-(2-oxo-1,2,5,6-tetrahydropyrid-1-yl)piperidino]butyl]-N-methylbenzamide hydrochloride.

Using a procedure similar to that described in Example 7, except replacing 4-(2-oxopyrrolidin-1-yl)piperidine with 4-(2-oxo-1,2,5,6-tetrahydropyrid-1-yl)piperidine and N-[2-(3,4-dichlorophenyl)- 4-oxobutyl]-N-methylbenzamide with (S)-N-[2-(3,4-dichlorophenyl)-4-oxobutyl]-N-methylbenzamide, the title compound was obtained as a white solid; MS: m/z=514(M+1). Analysis for C$_{28}$H$_{33}$Cl$_2$N$_3$O$_2$·2.50 HCl·0.30 Et$_2$O: Calculated: C, 55.86; H, 6.18; N, 6.69; Found: C, 55.83; H, 6.43; N, 6.66.

The intermediate 4-(2-oxo-1,2,5,6-tetrahydropyrid-1-yl)-piperidine was prepared as follows.

a. 1-Benzyloxycarbonyl-4-(2-oxo-3-phenylselenopiperidino)-piperidine. Butyllithium (27 mL, 1.6M in hexanes) was added dropwise to a stirred solution of diisopropylamine (6.1 mL) in tetrahydrofuran (100 mL) at −78° C. After 10 minutes, 1-benzyloxycarbonyl-4-(2-oxopiperidino)piperidine (9.8 g) in tetrahydrofuran (25 mL) was added dropwise. After 1 hour, a premixed solution of diphenyl diselenide (7.3 g) and bromine (1.2 mL) in tetrahydrofuran (25 mL) was added rapidly to the enolate solution via a polytetrafluoroethylene cannula. After being stirred for 45 minutes, the mixture was quenched with saturated aqueous ammonium chloride, allowed to warm to room temperature, and evaporated. The resulting aqueous solution was diluted with water, adjusted to pH of 7 with 0.4N hydrochloric acid, and extracted with dichloromethane. The organic extracts were dried, evaporated, and chromatographed, with ether- :dichloromethane (10:1) as the eluent. The resulting material was chromatographed again, with dichloromethane and then ether as the eluent, to give the title compound (9.2 g) as a light yellow, viscous oil; MS: m/z=473(M+1); NMR: 7.68 (m,2), 7.36 (m,4), 7.28 (m,4), 5.12 (s,2), 4.65 (m,1), 4.26 (m,2), 4.04 (m,1), 3.13 (m,2), 2.87 (m,2), 2.09 (m,1), 1.98 (m,2), 1.75–1.55 (m,5).

b. 1-Benzyloxycarbonyl-4-(2-oxo-1,2,5,6-tetrahydropyrid-1-yl)piperidine. To a stirred solution of 1-benzyloxycarbonyl-4-(2-oxo-3-phenylselenopiperidino)piperidine (9.0 g) in dichloromethane (80 mL) at −78° C. was added 3-chloroperoxybenzoic acid (4.1 g, 80–85%) in dichloromethane (20 mL). After 30 minutes, the reaction mixture was warmed to 0° C. and triethylamine (6.6 mL) was added. After 10 minutes, the mixture was washed (aqueous sodium bicarbonate, 0.4N hydrochloric acid, aqueous sodium bicarbonate), dried, and evaporated. The crude material was chromatographed, with dichloromethane:methanol (gradient 98:2, 90:10) as the eluent, to give the title compound (5.7 g) as a viscous oil; MS: m/z=315(M+1); NMR: 7.34 (m,5), 6.54 (dr,1, J=4.2, 9.7), 5.95 (dr,1, J=1.7, 9.7), 5.13 (s,2), 4.67 (m,1), 4.29 (m,2), 3.26 (t,2, J=7.0), 2.90 (m,2), 2.31 (m,2), 1.64 (m,4).

c. 4-(2-Oxo-1,2,5,6-tetrahydropyrid-1-yl)piperidine. Trifluoromethanesulfonic acid (1.4 mL) was added dropwise to a solution of 1-benzyloxycarbonyl-4-(2-oxo-1,2,5,6-tetrahydropyrid-1-yl)piperidine (1.6 g) in dichloromethane (20 mL) at 0° C. After being stirred for 15 minutes, the reaction mixture was diluted with water and extracted with dichloromethane (discarded). The acidic aqueous phase was adjusted to pH 10 with 10N sodium hydroxide and extensively extracted with dichloromethane. The organic extracts were dried and evaporated to give the title compound (540 mg) as a white solid; MS: m/z=181(M+1); NMR (CD$_3$OD): 6.68 (dt,1, J=4.2, 9.7), 5.86 (dt,1, J=1.8, 9.8), 4.47 (m,1), 3.39 (t,2, J=7.1), 3.09 (m,2), 2.66 (m,2), 2.36 (m,2), 1.68 (m,2), 1.61 (m,2).

EXAMPLE 22

The following illustrates representative pharmaceutical dosages forms which may be used for the therapeutic or prophylactic administration of a compound of formula I (or formula Ic), or the N-oxide of the piperidino nitrogen indicated by Δ, or a pharmaceutically acceptable salt thereof, or a quaternary ammonium salt thereof (hereinafter referred to as 'Compound X'):

| (i) | Tablet I | mg/tablet |
|---|---|---|
| | 'Compound X' | 100.0 |
| | Lactose | 77.5 |
| | Povidone | 15.0 |
| | Croscarmellose sodium | 12.0 |
| | Microcrystalline cellulose | 92.5 |
| | Magnesium stearate | 3.0 |
| | | 300.0 |
| (ii) | Tablet 2 | mg/tablet |
| | 'Compound X' | 20.0 |
| | Microcrystalline cellulose | 410.0 |
| | Starch | 50.0 |
| | Sodium starch glycolate | 15.0 |
| | Magnesium stearate | 5.0 |
| | | 500.0 |
| (iii) | Capsule | mg/capsule |
| | 'Compound X' | 10.0 |

| | | |
|---|---|---|
| | Colloidal silicon dioxide | 1.5 |
| | Lactose | 465.5 |
| | Pregelatinized starch | 120.0 |
| | Magnesium stearate | 3.0 |
| | | 600.0 |
| (iv) | Injection 1 (1 mg/mL) | mg/mL |
| | 'Compound X' (free acid form) | 1.0 |
| | Dibasic sodium phosphate | 12.0 |
| | Monobasic sodium phosphate | 0.7 |
| | Sodium chloride | 4.5 |
| | 1.0 N Sodium hydroxide solution (pH adjustment to 7.0–7.5) | q.s. |
| | Water for injection | q.s. ad 1 mL |
| (v) | Injection 2 (10 mg/mL) | mg/mL |
| | 'Compound X' (free acid form) | 10.0 |
| | Monobasic sodium phosphate | 0.3 |
| | Dibasic sodium phosphate | 1.1 |
| | Polyethylene glycol 400 | 200.0 |
| | 0.1 N Sodium hydroxide solution (pH adjustment to 7.0–7.5) | q.s. |
| | Water for injection | q.s. ad 1 mL |
| (vi) | Aerosol | mg/can |
| | 'Compound X' | 20.0 |
| | Oleic acid | 10.0 |
| | Trichloromonofluoromethane | 5,000.0 |
| | Dichlorodifluoromethane | 10,000.0 |
| | Dichlorotetrafluoroethane | 5,000.0 |

It will be appreciated that the above pharmaceutical compositions may be varied according to well-known pharmaceutical techniques to accomodate differing amounts and types of active ingredient 'Compound X'. The aerosol (vi) may be used in conjunction with a standard, metered dose aerosol dispenser.

FORMULAE

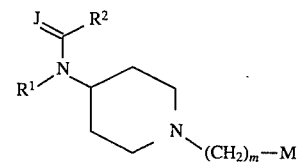

I

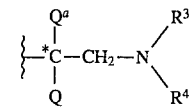

Ia

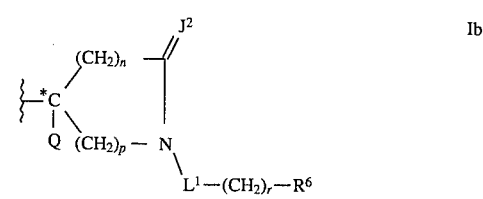

Ib

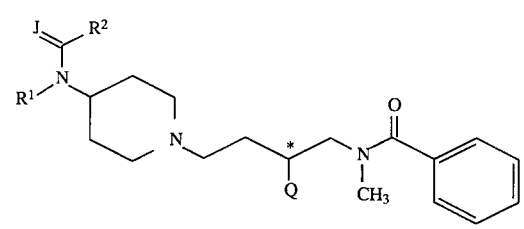

Ic

33
-continued
FORMULAE

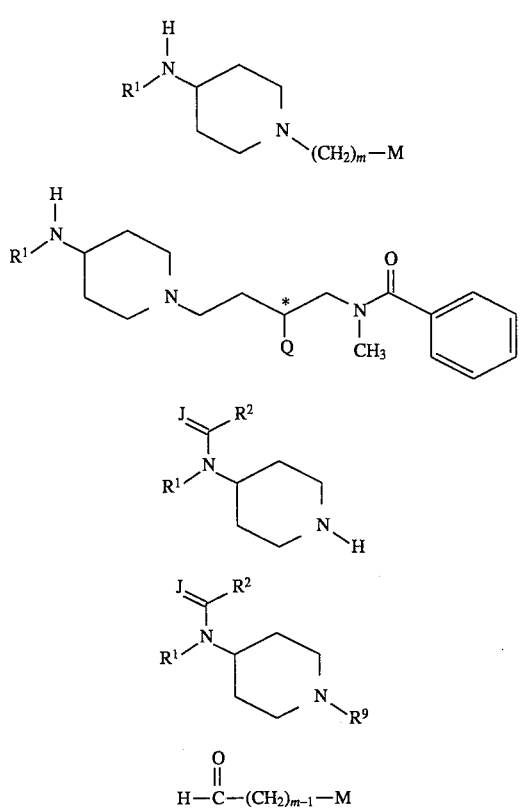

34
-continued
FORMULAE

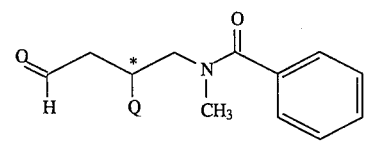

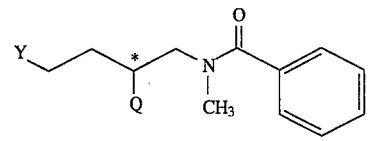

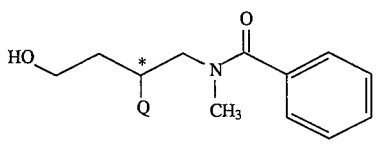

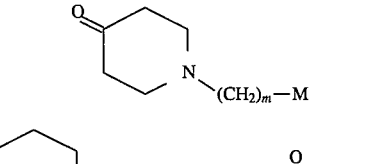

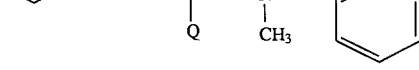

---

What is claimed is:

1. A compound of formula I:

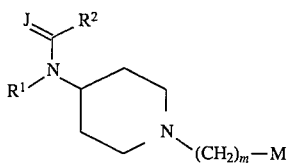

wherein

J is oxygen, sulfur or NR$^n$ in which R$^n$ is hydrogen or (1-3C)alkyl;

R$^1$ is hydrogen, (1-6C)alkyl, (3-6C)alkenyl (in which a vinyl carbon is not bound to nitrogen), 2-hydroxyethyl, or (3-7C)cyloalkyl;

R$^2$ is hydrogen, (1-6C)alkyl which may bear a hydroxy substituent and/or one to three fluoro substituents, (3-6C)cycloalkyl, (1-5C)alkoxy (only when J is oxygen), (3-6C)cycloalkyloxy (only when J is oxygen), or an amino group of formula NR$^a$R$^b$ containing zero to about seven carbon atoms in which each of R$^a$ and R$^b$ is independently hydrogen, (1-5C)alkyl or (3-6C)cycloalkyl, or R$^a$ and R$^b$ together with the nitrogen to which they are attached form a pyrrolidino, piperidino, morpholino, thiomorpholino (or its S-oxide) or piperazinyl group (which piperazinyl group may bear a methyl or ethyl group at the 4-position);

m is 2 or 3;

M is a residue of formula Ia or formula Ib:

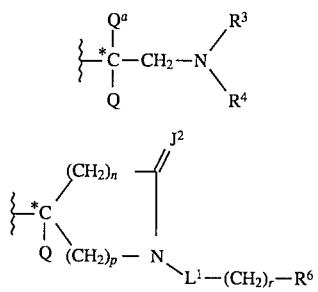

wherein

Q is phenyl which may bear one or two substituents independently selected from halo, trifluoromethyl, hydroxy, (1-3C)alkoxy, (1-3C)alkyl and methylenedioxy; or Q is thienyl, imidazolyl, benzo[b]thiophenyl or naphthyl any of which may bear a halo substituent; or Q is biphenylyl; or Q is carbon-linked indolyl which may bear a benzyl substituent at the 1-position;

Q$^a$ is hydrogen, (1-4C)alkyl, or a radical of formula —(CH$_2$)$_q$—NR$^7$R$^8$ in which q is 2 or 3 and R$^7$ and R$^8$ are independently (1-4C)alkyl or NR$^7$R$^8$ is piperidino or 4-benzylpiperidino;

R$^3$ is hydrogen, methyl or (2-6C)n-alkyl which may bear a terminal amino radical;

R$^4$ is —COR$^5$, —COOR$^5$ or —C(=J$^1$)NHR$^5$ in which J$^1$ is oxygen or sulfur and R$^5$ is hydrogen, (1-6C)alkyl, phenyl(1-3C)alkyl (in which the phenyl may bear one or more halo, hydroxy, (1-4C)alkoxy or (1-4C)alkyl substituents), pyridyl(1-3 C)alkyl, naphthyl(1-3C)alky pyridylthio(1-3C)alkyl, styryl, 1-methylimidazol-2-ylthio(1-3C)alkyl, aryl (which may bear one or more halo, hydroxy, (1-4C)alkoxy or (1-4C)alkyl substituents), heteroaryl (which may bear one or more halo, hydroxy, (1-4C)alkoxy or (1-4C)alkyl substituents), or (when R$^4$ is —COR$^5$) α-hydroxybenzyl;

n is 0, 1, 2 or 3;

p is 1 or 2, and when p is 2, n is 1 and J$^2$ is two hydrogens;

J$^2$ is oxygen or two hydrogens;

L$^1$ is carbonyl or methylene;

r is 0, 1, 2, or 3; and

R$^6$ is phenyl which may bear one or more halo, trifluoromethyl, (1-4C)alkyl, hydroxy or (1-4C)alkoxy substituents; naphthyl which may bear one or more halo, trifluoromethyl, (1-4C)alkyl or hydroxy substituents; pyridyl; thienyl; indolyl; quinolinyl; benzothienyl or imidazolyl; or when L$^1$ is carbonyl, the group —(CH$_2$)$_r$—R$^6$ may represent a benzyl group bearing an α-substituent selected from hydroxy, (1-4C)alkoxy and (1-4)alkyl, wherein the phenyl portion of the benzyl group may bear one or more substituents selected independently from halo, trifluoromethyl, (1-4C)alkyl, hydroxy and (1-4C)alkoxy;

or the N-oxide of the piperidino nitrogen indicated by Δ;

or a pharmaceutically acceptable salt thereof;

or a quaternary ammonium salt thereof in which the piperidino nitrogen indicated by Δ is a quadricovalent ammonium nitrogen wherein the fourth radical on the nitrogen R$^9$ is (1-4C)alkyl or benzyl and the associated counterion A is a pharmaceutically acceptable anion.

2. A compound of formula I as claimed in claim 1 wherein,

M is a residue of formula Ib;

or the N-oxide of the piperidino nitrogen indicated by Δ;

or a pharmaceutically acceptable salt thereof;

or a quaternary ammonium salt thereof in which the piperidino nitrogen indicated by Δ is a quadricovalent ammonium nitrogen wherein the fourth radical on the nitrogen R$^9$ is (1-4C)alkyl or benzyl and the associated counterion A is a pharmaceutically acceptable anion.

3. A compound as claimed in claim 1 which is a compound of formula Ic:

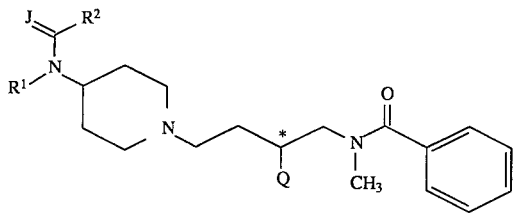

or the N-oxide of the piperidinio nitrogen indicated by Δ;

or a pharmaceutically acceptable salt thereof;

or a quaternary ammonium salt thereof; wherein J, R$^1$, R$^2$, Q, R$^9$ and A have any of the values defined in claim 1.

4. A compound as claimed in claim 2 in which

J is oxygen, sulfur, imino, methylimino or ethylimino;

R$^1$ is hydrogen, methyl, ethyl, propyl, isopropyl, butyl, hexyl, allyl or cyclohexyl; R$^2$ is hydrogen, methyl, trifluoromethyl, ethyl, propyl, isopropyl, methylamino or dimethylamino;

m is 2;

n is 1 or 2; p is 1; J$^2$ is two hydrogens; L$^1$ is carbonyl; r is 0 or 1; R$^6$ is phenyl which may bear one or two halo or (1-4C)alkoxy substituents; and Q is phenyl which may bear one or two substituents selected from halo, trifluoromethyl and methylenedioxy;

or the N-oxide of the piperidino nitrogen indicated by Δ;

or a pharmaceutically acceptable salt thereof;

or a quaternary ammonium salt thereof in which the piperidino nitrogen indicated by Δ is a quadricovalent ammonium nitrogen wherein the fourth radical on the nitrogen $R^9$ is methyl or benzyl; and the associated counterion A is chloride, bromide or methanesulfonate.

5. A compound as claimed in claim 4 in which

J is oxygen or sulfur;

$R^6$ is phenyl which may bear a chloro, fluoro or isopropoxy substituent; and

Q is 3,4-dichlorophenyl or 3,4-methylenedioxyphenyl;

or a pharmaceutically acceptable salt thereof.

6. A compound as claimed in claim 1 in which

J is oxygen, sulfur, imino, methylimino or ethylimino;

$R^1$ is hydrogen, methyl, ethyl, propyl, isopropyl, butyl, hexyl allyl or cyclohexyl; $R^2$ is hydrogen, methyl, trifluoromethyl, ethyl, propyl, isopropyl, methylamino or dimethylamino;

M is a residue of formula Ia;

m is 2;

Q is phenyl which may bear one or two substituents selected from halo, trifluoromethyl and methylenedioxy; and $Q^a$ is hydrogen, $R^3$ is methyl; is $R^4$—$COR^5$; $R^5$ is aryl which aryl may bear one or two chloro or fluoro substituents;

or the N-oxide of the piperidino nitrogen indicated by Δ;

or a pharmaceutically acceptable salt thereof;

or a quaternary ammonium salt thereof in which the piperidino nitrogen indicated by Δ is a quadricovalent ammonium nitrogen wherein the fourth radical on the nitrogen $R^9$ is methyl or benzyl; and the associated counterion A is chloride, bromide or methanesulfonate.

7. A compound as claimed in claim 6 in which

J is oxygen or sulfur;

$R^5$ is phenyl, which phenyl may bear one or two chloro or fluoro substituents; and Q is 3,4-dichlorophenyl or 3,4-methylenedioxyphenyl;

or a pharmaceutically acceptable salt thereof.

8. A compound as claimed in claim 3 in which

J is oxygen;

Q is 3,4-dichlorophenyl;

$R^1$ is hydrogen, (1-6C)alkyl, 2-hydroxyethyl, (3-7C)cycloalkyl; and $R^2$ is hydrogen, (1-6C)alkyl which may bear a hydroxy substituent and/or one to three fluoro substituents, (3-6C)cycloalkyl, (1-5C)alkoxy, (3-6C)cycloalkyloxy or an amino group of formula $NR^aR^b$ containing zero to about seven carbon atoms in which each of $R^a$ and $R^b$ is independently hydrogen, (1-5C)alkyl or (3-6C)cycloalkyl, or $R^a$ and $R^b$ together with the nitrogen to which they are attached form a pyrrolidino, piperidino, morpholino, thiomorpholino (or its S-oxide) or piperazinyl group, which piperazinyl group may bear a methyl or ethyl group at the 4-position;

or a pharmaceutically acceptable salt thereof.

9. A compound as claimed in claim 1 which is:

N-[4-(4-Acetamidopiperidino)-2-(3,4-dichlorophenyl)butyl]-N-methylbenzamide; N-[2-(3,4-Dichlorophenyl)-4-[4-(H-ethylacetamido)-piperidino] butyl]-H-methylbenzamide; N-[4-[4-(N-Butylacetamido)-piperidino]-2-(3,4-dichloro-phenyl)butyl]-N-methylbenzamide; N-[4-[4-(N-Cyclohexylacetamido)piperidino]-2-(3,4-dichlorophenyl)-butyl]-N-methylbenzamide; N-[2-(3,4-Dichlorophenyl)-4-[4-(N-hexylacetamido)-piperidino]butyl]-N-methylbenzamide; N-[2-(3,4-Dichlorophenyl)-4-[4-(N-methylacetamido)-piperidino]butyl]-N-methylbenzamide; N-[4-[4-(N-Allylacetamido)-piperidino]-2-(3,4-dichloro-phenyl)butyl]-N-methylbenzamide; N-[2-(3,4-Dichlorophenyl)-4-[4-(N-propylacetamido)-piperidino]-butyl]-N-methylbenzamide; N-[2-(3,4-Dichlorophenyl)-4-[4-(N-isopropylacetamido)piperidino]butyl]-N-methylbenzamide; N-[2-(3,4-Dichlorophenyl)-4-[4-(N-ethylpropionamido)piperidino]butyl]-N-methylbenzamide; N-[2-(3,4-Dichlorophenyl)-4-[4-(N-ethylbutyramido)-piperidino]butyl]-N-methylbenzamide; N-[2-(3,4-Dichlorophenyl)-4-[4-(N-ethylisobutyramido)-piperidino]butyl]-N-methylbenzamide; N-[2-(3,4-Dichlorophenyl)-4-[4-(N-ethyltrifluoroacetamido)piperidino]-butyl]-N-methylbenzamide; N-[2-(3,4-Dichlorophenyl)-4-[4-(N-ethyl-N'-methylureido)-piperidino]butyl]-N-methylbenzamide; N-[2-(3,4-Dichlorophenyl)-4-[4-(N-ethyl-N',N'-dimethyl-ureido)piperidino]butyl]-N-methylbenzamide; or N-[2-(3,4-Dichlorophenyl)-4-[4-(N-ethylformamido)-piperidino]butyl]-N-methylbenzamide; in either the racemic form or as the (S)-enantiomeror;

or a pharmacologically acceptable salt thereof.

10. A method of treating asthma in a human or other mammal, comprising: administering an effective dose of a compound selected from claim 1 or a pharmaceutically acceptable salt thereof.

11. A pharmaceutical composition comprising a compound of formula I or the N-oxide of the piperidino nitrogen indicated by Δ, or a pharmaceutically acceptable salt thereof, or a quaternary ammonium salt thereof, selected from claim 1, and a pharmaceutically acceptable diluent or carrier.

* * * * *

UNITED STATES PATENT AND TRADEMARK OFFICE
CERTIFICATE OF CORRECTION

PATENT NO. : 5,559,132
DATED : September 24, 1996
INVENTOR(S) : Scott Carson Miller It is certified that error appears in the above-indentified patent and that said Letters Patent is hereby corrected as shown below:

Column 35, line 5, formula I:

"

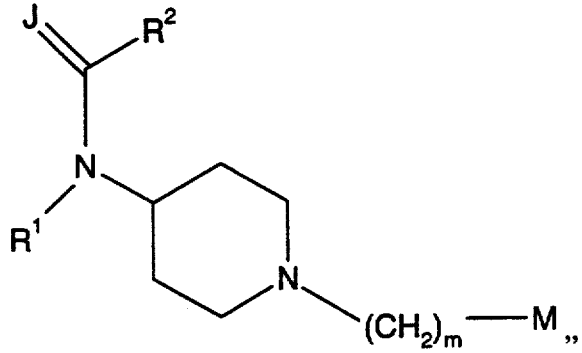

should read

--

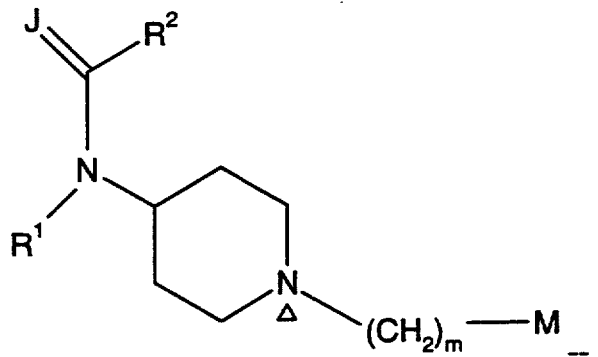

--.

Column 35, line 61, "naphthyl(1-3C)alky" should read -- naphthyl(1-3C)alkyl,--.

UNITED STATES PATENT AND TRADEMARK OFFICE
CERTIFICATE OF CORRECTION

PATENT NO. : 5,559,132
DATED : September 24, 1996
INVENTOR(S) : Scott Carson Miller It is certified that error appears in the above-indentified patent and that said Letters Patent is hereby corrected as shown below:

Column 36, line 40, formula Ic:

"

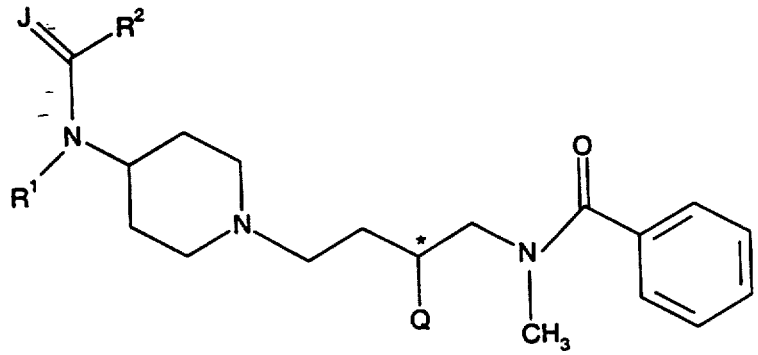

should read

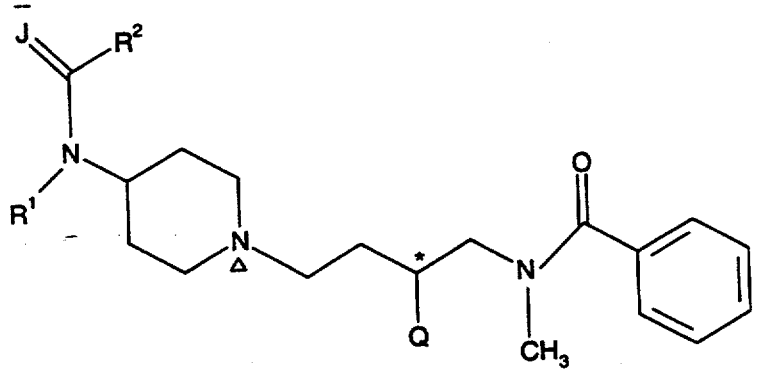

"

UNITED STATES PATENT AND TRADEMARK OFFICE
CERTIFICATE OF CORRECTION

PATENT NO. : 5,559,132
DATED : September 24, 1996
INVENTOR(S) : Scott Carson Miller It is certified that error appears in the above-indentified patent and that said Letters Patent is hereby corrected as shown below:

Column 37, line 17, "hexyl allyl" should read --hexyl, allyl--.

Column 37, line 26, "$Q^a$ is hydrogen, $R^3$ is methyl; is" should read -- $Q^a$ is hydrogen, $R^3$ is methyl;--.

Column 37, line 27, "$R^4$ -$COR^5$;" should read -- $R^4$ is -$COR^5$;--.

Column 38, line 11, "(H-ethylacetamido)-piperidino]butyl]-H-" should read --(N-ethylacetamido)-piperidino]butyl]-N---.

Signed and Sealed this

Twenty-fourth Day of December, 1996

Attest:

BRUCE LEHMAN

Attesting Officer

Commissioner of Patents and Trademarks